United States Patent
Chaiken et al.

(10) Patent No.: US 8,575,095 B2
(45) Date of Patent: Nov. 5, 2013

(54) ACTIVE CORES OF PEPTIDE TRIAZOLE HIV-1 ENTRY INHIBITORS

(75) Inventors: Irwin M. Chaiken, Philadelphia, PA (US); Umashankara Muddegowda, Philadelphia, PA (US); Karyn McFadden, Philadelphia, PA (US)

(73) Assignee: Philadelphia Health & Education Corporation, Philadelphia, PA (US)

( * ) Notice: Subject to any disclaimer, the term of this patent is extended or adjusted under 35 U.S.C. 154(b) by 5 days.

(21) Appl. No.: 13/380,422

(22) PCT Filed: Jun. 24, 2010

(86) PCT No.: PCT/US2010/039829
§ 371 (c)(1),
(2), (4) Date: Mar. 12, 2012

(87) PCT Pub. No.: WO2010/151675
PCT Pub. Date: Dec. 29, 2010

(65) Prior Publication Data
US 2012/0165250 A1    Jun. 28, 2012

Related U.S. Application Data

(60) Provisional application No. 61/220,134, filed on Jun. 24, 2009.

(51) Int. Cl.
*A61K 38/04*   (2006.01)
*A61K 38/08*   (2006.01)

(52) U.S. Cl.
USPC ............ 514/3.8; 530/329; 530/328; 530/400; 514/1.1; 514/21.7

(58) Field of Classification Search
USPC ........................................................ 514/3.8
See application file for complete search history.

(56) References Cited

U.S. PATENT DOCUMENTS

2006/0135746 A1   6/2006   Hosahudya et al.

FOREIGN PATENT DOCUMENTS

WO   2008/150444   12/2008

OTHER PUBLICATIONS

Gopi et al., J. Mol. Recognit. (2009, published online May 22, 2008) 22: 169-174.*
Cocklin et al., "Broad-Spectrum Anti-Human Immunodeficiency Virus (HIV) Potential of a Peptide HIV Type 1 Entry Inhibitor," *Journal of Virology*, Apr. 2007, 81(7):3645-3648.
Ferrer et al., "Peptide Ligands to Human Immunodeficiency Virus Type 1 gp120 Identified from Phage Display Libraries," *Journal of Virology*, Jul. 1999, 73(7):5795-5802.
Gopi et al., "Click Chemistry on Azidoproline: High-Affinity Dual Antagonist for HIV-1 Envelope Glycoprotein gp120," *ChemMedChem*, 2006, 1:54-57.
Tsai et al., "Cyanovirin-N. Gel as a Topical Microbicide Prevents Rectal Transmission of SHIV89.6P in Macaques," *Aids Research and Human Retroviruses*, 2003, 19(7):535-541.
Tsai et al., "Cyanovirin-N. Inhibits AIDS Virus Infections in Vaginal Transmission Models," *Aids Research and Human Retroviruses*, 2004, 20(1):11-18.
Boyd et al., "Discovery of Cyanovirin-N, a Novel Human Immunodeficiency Virus-Inactivating Protein That Binds Viral Surface Envelope Glycoprotein gp120: Potential Applications to Microbicide Development," *Antimicrobial Agents and Chemotherapy*, Jul. 1997, 41(7):1521-1530.
International Preliminary Report on Patentability dated Jan. 4, 2012 for PCT/US10/39829.

* cited by examiner

*Primary Examiner* — Karlheinz R Skowronek
*Assistant Examiner* — Catherine Mader
(74) *Attorney, Agent, or Firm* — Riverside Law LLP

(57) ABSTRACT

The invention provides a peptide triazole conjugate and derivatives thereof, and methods of its use. Further provided are an antibody to the peptide triazole conjugate, and a method of identifying an HIV-1 entry inhibitor candidate.

31 Claims, 20 Drawing Sheets

FIGURE 1B
| Conjugate | Structure of R group | Radical Name |
|---|---|---|
| HNG-113 | 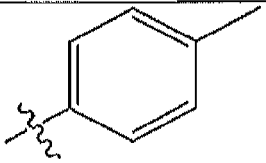 | *p*-tolyl |
| HNG-124 | 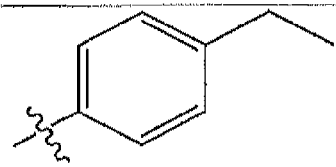 | 4-ethylphenyl |
| HNG-125 | 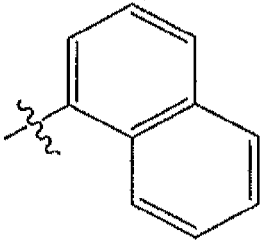 | Naphthylene-1-yl |
| HNG-137 | 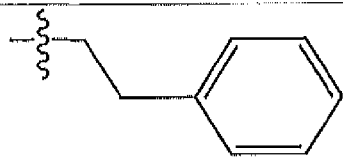 | phenylethyl |

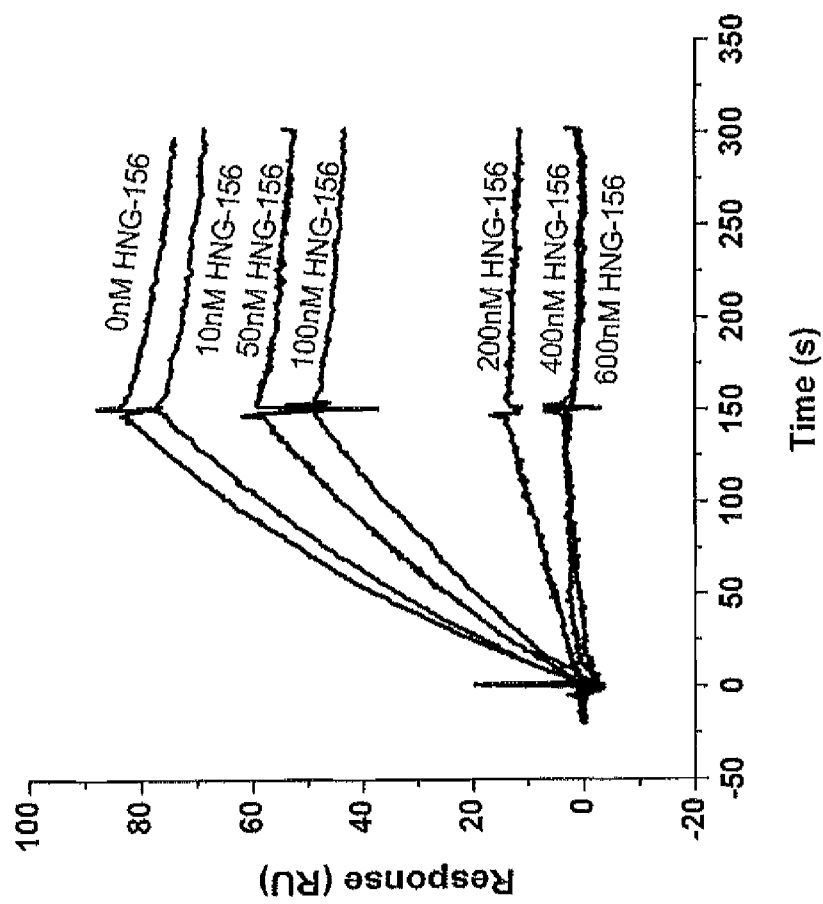

FIGURE 9A

| Peptide | Structure | Mass Calculated | Mass Obtained | IC50 nM CD4 | IC50 nM 17b | IC50 µM (viral) |
|---|---|---|---|---|---|---|
| UM10 | Azp-W-S-E-A-M-M | 1056.44 | 1100.26 (M+K) | NA | NA | NA |
| UM11 | R-I-N-N-I-Azp-W-S | 1249.54 | 1249.4 (M+) | 85 | 168 | 10.7±4.7 |
| UM12 | R-I-N-N-I-Azp-W | 1125.17 | 1125.62 (M+) | 124 | 218 | 12.5±0.6 |
| UM13 | E-I-N-N-I-Azp-W-S | 1178.67 | 1179.31 (M+) | 79 | 154 | 3.2±0.9 |
| UM15 | I-N-N-I-Azp-W | 1005.43 | 1005.74 (M+) | 133 | 241 | 7.2 |
| UM16 | R-I-N-N-I-Azp | 979.45 | 979.52 (M+) | NA | NA | NA |
| UM21 | I-N-N-I-Azp-W-S | 1091.54 | 1092.41 (M+) | 86 | 161 | 7.4±2.7 |
| UM22 | R-N-N-I-Azp-W-S | 1136.41 | 1137.27 (M+) | 123 | 181 | ND |
| UM23 | E-N-N-I-Azp-W-S | 1121.5 | 1122.2 (M+) | 88 | 165 | 6.6 |
| UM24 | Ct-N-N-I-Azp-W-S | 1135.54 | 1137.14 (M+2) | 81 | 152 | 4.9±0.8 |
| UM27 | K-N-N-I-Azp-W-S | 1107.09 | 1108.15 (M+) | 128 | 197 | ND |
| UM28 | F-N-N-I-Azp-W-S | 1125.52 | 1126.41 (M+) | 105 | 174 | 11 |
| UM31 | N-N-I-Azp-W-S | 979.38 | 979.4 (M+) | 5X10$^5$ | 16X10$^3$ | 10 |
| UM35 | I-N-I-Azp-W-S | 978.42 | 978.2 (M+) | ND | ND | 17 |

NA = not active; ND = not determined
M+ = mass; M+K = mass + one molecule potassium; M+2 = mass + 2 molecules hydrogen

FIGURE 9B

| Conjugate Designation | SEQ ID No. for peptide | Peptide Sequence | Mass (Da) Observed[a] | Mass (Da) Calculated |
|---|---|---|---|---|
| HNG-156 | 16 | R-I-N-N-I-Azp-W-S-E-A-M-M | 1711.32 | 1711.4 |
| N- and C- terminal Truncates | | | | |
| UM-10 | 19 | Azp-W-S-E-A-M-M | 1100.36[b] | 1056.26 |
| UM-12 | 7 | R-I-N-N-I-Azp-W | 1162.5 | 1161.53 |
| Side chain Variation in first residue | | | | |
| UM11 | 5 | R-I-N-N-I-Azp-W-S | 1249.4 | 1249.54 |
| UM13 | 6 | E-I-N-N-I-Azp-W-S | 1235.5 | 1222.5 |
| Side chain Variation in second residue | | | | |
| UM21 | 4 | I-N-N-I-Azp-W-S | 1092.41 | 1091.54 |
| UM22 | 8 | R-N-N-I-Azp-W-S | 1137.27 | 1136.41 |
| UM23 | 9 | E-N-N-I-Azp-W-S | 1122.53 | 1121.5 |
| UM24 | 10 | Cit-N-N-I-Azp-W-S | 1136.6 | 1135.54 |
| UM27 | 11 | K-N-N-I-Azp-W-S | 1107.5 | 1107.09 |
| UM28 | 12 | F-N-N-I-Azp-W-S | 1126.5 | 1125.52 |
| Side Chain Variation in Third residue | | | | |
| UM31 | 14 | N-N-I-Azp-W-S | 979.4 | 979.38 |
| UM32 | 23 | R-N-I-Azp-W-S | 1022.5 | 1021.43 |
| UM33 | 24 | E-N-I-Azp-W-S | 994.4 | 994.37 |
| UM34 | 25 | Cit-N-I-Azp-W-S | 1022.2 | 1022.42 |
| UM-35 | 15 | I-N-I-Azp-W-S | 978.23 | 978.42 |
| Active Pharmacophore sequence | | | | |
| UM15 | 13 | I-N-N-I-Azp-W | 1005.5 | 1005.43 |
| UM16 | 20 | R-I-N-N-I-Azp | 976.3 | 978.45 |
| UM17 | 21 | N-N-I-Azp-W | 892.05 | 892.34 |
| UM41 | 22 | N-I-Azp-W-S | 865.0[c] | 849.76 |
| Stereochemistry importance for Trp residue | | | | |
| UM24-DW | n/a | Cit-N-N-I-Azp-W[D]-S | 1137.14 | |

11A

11B

13B

13A

ACTIVE CORES OF PEPTIDE TRIAZOLE HIV-1 ENTRY INHIBITORS

STATEMENT REGARDING FEDERALLY SPONSORED RESEARCH OR DEVELOPMENT

This invention was made with government support under grant numbers P01 GM056550 and R21 A1071965 awarded by the National Institutes of Health and contract number GPO-A-00-05-00041-00 awarded by the U.S. Agency for International Development (USAID), subcontract from IPM. The Government therefore has certain rights in this invention.

CROSS-REFERENCE TO RELATED APPLICATIONS

The present application is a 35 U.S.C. §371 national phase application from, and claiming priority to, International Application No. PCT/US2010/039829, filed Jun. 24, 2010, and published under PCT Article 21(2) in English, which is entitled to priority under 35 U.S.C. §119(e) to U.S. Provisional Application No. 61/220,134, filed Jun. 24, 2009, which applications are incorporated by reference herein in their entireties.

BACKGROUND OF THE INVENTION

Acquired immunodeficiency syndrome (AIDS), the pandemic infection caused by human immunodeficiency virus-1 (HIV-1), has created an urgent need for new classes of antiviral agents. HIV-1 has infected over 60 million and killed over 20 million individuals worldwide since the beginning of the epidemic (WHO/UNAIDS, December 2005, AIDS Epidemic Update).

HIV infection is not curable. To date, there is no HIV vaccine. There are currently four classes of therapeutics for HIV treatment: nucleoside reverse transcriptase inhibitors, non-nucleoside transcriptase inhibitors, protease inhibitors and fusion inhibitors. Fusion inhibition, which blocks interaction of virus with either or both host cell receptors, is considered to be one of the most effective approaches to prevent and inhibit viral infections. To date, very few fusion inhibitors have been identified.

The primary targets for HIV-1 infection in vivo are CD4$^+$ T cells and cells of the monocyte/macrophage lineage (Klatzmann et al., 1984, Nature 312: 767-8; Dalgleish et al., 1984, Nature 312: 763-7). The initial, critical step of HW infection is its cell entry through the fusion of the viral membrane with the membrane of either a T-cell or macrophage. Major advances have been made over the past decade in the understanding of the molecular machinery of HIV entry into these target cells. An initial step in the entry process is the interaction of the external HIV envelope glycoprotein, gp120, with T-cell CD4 receptor molecules. The functional HIV-1 envelope complex is a trimeric structure comprising three gp120 surface glycoproteins, each noncovalently attached to one of three subunits of the gp41 transmembrane glycoproteins (Chan et al., 1997, Cell 89: 263-73; Wyatt et al., 1998, Science 280: 1884-8; Tan et al., 1997, Proc Natl Acad Sci USA 94: 12303-8). Recent crystal structures of gp120-CD4 with co-receptor surrogate antibody complexes have provided insights into the formation of protein-protein interactions in the process of viral entry (Kwong et al., 1998, Nature 393: 648-59; Huang et al., 2005, Structure 13: 755-68; Huang et al., 2005, Science 310: 1025-8). The binding of gp120 to CD4 receptor promotes a conformational rearrangement in the envelope gp120, that creates a new site for binding of another co-receptor, CCR5 or CXCR4 (Wu et al, 1996, Nature 384: 179-83; Dragic et al., 1996, Nature 381: 667-73). The interaction of virus envelope gp120-CD4 complex with co-receptor is believed to promote further conformational rearrangements in HIV-1 envelope that drive fusion of the viral and host cell membranes. Blocking the binding of CD4 with gp120 or preventing the CD4-induced conformational isomerization that promotes co-receptor binding and viral cell fusion are believed to have great potential for the prevention and treatment of HIV-1 infection and AIDS.

Currently, the development of effective HIV entry inhibitors are mainly focused on natural ligands (Doranz et al., 1997, Immunol Res 16: 15-28; Munk et al., 2003, AIDS Res Hum Retroviruses 19: 875-81), monoclonal antibodies (Gallo et al., 2006, J Biol Chem 281: 18787-92; Zhang et al., 2007, Curr Pharm Des 13: 203-12; Cardoso et al., 2005, Immunity 22: 163-73; Zhang et al., 2003, J Immunol Methods 283: 17-25), and small synthetic compounds, obtained either by high-throughput screening of large compound libraries (Lin et al., 2003, Proc Natl Acad Sci USA 100: 11013-8; Zhao et al., 2005, Virology 339: 213-25; Ferrer et al., 1999, J Virol 73: 5795-802) or structure-guided rationally-designed compounds that interfere with gp120/CD4 or co-receptor interaction (Vita et al., 1999, Proc Natl Acad Sci USA 96: 13091-6; DeMarco et al., 2006, Bioorg Med Chem 14: 8396-404).

Recent investigations using both in vitro and in vivo assays have demonstrated the potential topical microbiocide activity of cyanovirin-N (CV-N), an 11 kD protein originally isolated from the cyanobacteria *Nostoc ellipsosporum* (Boyd et al., 1997, Antimicro Agents Chemother. 41:1521-1530), CV-N inactivates a broad range of M-tropic and T-tropic strains of HIV-1, SIV, FIV and prevents cell-to-cell transmission of infection (Boyd et al., 1997, Antimicro Agents Chemother. 41; 1521-1530). CV-N binds specifically to the highly glycosylated viral envelope protein gp120 and to the functionally analogous SIV proteins sgp130 and sgp140. The epitopes on gp120 responsible for CV-N binding appear to be predominantly high-mannose glycosylation sites of the envelope. Recombinant CV-N blocks HIV-1 BaL infection of human ectocervical explants without cytotoxic effects (Tsai et al., 2004, AIDS Res Hum Retroviruses 20:11-18). Gel formulations of CVN applied rectally to male macaques protected against challenge by the SIV/HIV-1 virus SHIV89.6P (Tsai et al, 2003, AIDS Res Hum Retroviruses 19:535-541). In vivo efficacy has also be shown in a vaginal challenge model with female macaques (Tsai et al., 2004, AIDS Res Hum Retroviruses 20:11-18). CV-N showed no clinically adverse effects in these in vivo assays. However, the production costs and consequent cost per dose are limitations of the usage of CV-N alone as a therapeutic.

A screen of a random peptide phage-display library identified several peptides that bind to HIV-1 envelope glycoprotein gp120 (Ferrer et al., (1999, Virol. 73:5795-5802). One 12-mer, named 12p1, was found to inhibit the interaction between gp120 and four-domain soluble CD4 (4dCD4) and between gp120 and 17b, an HIV neutralizing monoclonal antibody. Recently, a derivative of 12p1, named HNG-105, obtained using a stable and chemically accessible azidoproline residue as a basis for side-chain bioconjugation reactions through click chemistry has been reported (U.S. Pat. Publication No. 20060135746; Gopi et al., 2006, ChemMedChem 1:54-57). Specifically, proline 6 of the 12p1 peptide was replaced with (2S,4S)-4-(4-phenyl-1H-1,2,3-triazol-1-yl) pyrrolidine-2-carboxylic acid. The resulting derivative, HNG-105, has a greater binding affinity for gp120, compared to 12p1, and also inhibits strongly the interaction between gp120 and both CD4 and 17b. Furthermore, HNG-105 showed inhibitory effects over a wide range of HIV-1 clades (Cocklin et al., 2007, J Viol, 81:3645-3648). HNG-105 inhibited viral infection with $IC_{50}$ values ranging from about 105 nM to about 865 nM.

There are currently over twenty medications approved for HIV-1 treatment, only two of which are fusion inhibitors. The development of drug resistant HIV is an on-going problem. Thus, there is a need for new HIV therapeutics. This invention addresses this need.

BRIEF SUMMARY OF THE INVENTION

In one aspect, the invention provides a peptide triazole conjugate comprising a peptide component comprising the sequence $X_1X_2X_3NIPWX_4$ (SEQ ID NO. 3), wherein optionally $X_1$, $X_1X_2$ and $X_4$ are each independently absent; the proline in SEQ ID NO. 3 is modified according to Formula I:

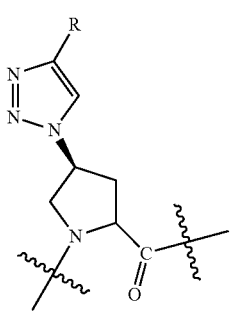

Formula I and R is a bulky aromatic group.

In another aspect, the invention provides a pharmaceutical composition comprising the peptide triazole conjugate and a pharmaceutically acceptable carrier. In an embodiment, the pharmaceutical composition further comprises cyanovirin-N or a functional derivative thereof. Optionally, the peptide triazole conjugate is covalently linked to the cyanovirin-N or functional derivative thereof. In an embodiment, the N-terminal residue of the peptide triazole conjugate is covalently linked to the C-terminal residue of the cyanovirin-N or functional derivative thereof. In some embodiments, the pharmaceutical composition can be formulated for topical or parenteral administration.

In another aspect, the invention also provides a method of treating HIV. The method comprises administering a therapeutically effective amount of the peptide triazole conjugate to an individual diagnosed with HIV. The invention further provides a method of reducing the risk of HIV infection. The method comprises administering a therapeutically effective amount of the peptide triazole conjugate to an individual at risk of HIV exposure.

In some embodiments, the bulky aromatic group of the peptide triazole conjugate is selected from the group consisting of a naphthyl group; a para-alkyl-substituted phenyl, wherein the alkyl is methyl or ethyl; 2-phenylethyl; and a metallocene. In a preferred embodiment, the bulky aromatic group is a metallocene. In another preferred embodiment, the metallocene is ferrocene.

In an embodiment, $X_1$ of SEQ ID No. 3 of the peptide triazole conjugate is selected from R and E. In an embodiment, $X_2$ is I and $X_3$ is N.

In another embodiment, $X_1$ is absent and $X_2$ is selected from the group consisting of I, F, K, E, R and Cit. In an embodiment, $X_3$ is N.

In another embodiment, $X_4$ of SEQ ID No. 3 is S or T.

In another embodiment, the sequence $X_1X_2X_3NIPWX_4$ is a sequence selected from the group consisting of: SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15 and SEQ ID No. 16.

In yet another embodiment, $X_1$, $X_1X_2$ and $X_4$ are absent and $X_3$ is N or I. In one embodiment, the peptide component is SEQ ID No. 21.

In another embodiment, the peptide component of the peptide triazole conjugate consists essentially of SEQ ID NO. 3 comprising the modified proline.

In yet another aspect, a method of isolating a viral envelope protein gp120 is provided. The method comprises a solid phase matrix with a sample comprising gp120, wherein a peptide triazole conjugate of the invention is linked to the solid phase matrix and wherein the gp120 binds to the peptide triazole conjugate thereby partitioning the sample into a bound phase and an unbound phase. The method further comprises separating the unbound phase from the unbound phase, thereby isolating the gp120.

The invention further provides an antibody to a peptide triazole conjugate of the invention in another aspect.

Further provided in yet another aspect is a method of identifying a HIV-1 entry inhibitor candidate, the method comprising the steps of assessing binding of a peptide triazole conjugate to gp120 in the presence and absence of a candidate molecule, wherein a molecule that reduces binding of the conjugate to gp120 is identified as an HIV-1 entry inhibitor candidate. The method optionally can further comprise assessing whether the candidate has dual antagonist activity by assessing binding of sCD4 and/or mAB 17b to gp120 in the presence and absence of the candidate molecule. The method can also optionally further comprise assessing antiviral activity of the candidate moiety.

BRIEF DESCRIPTION OF THE DRAWINGS

FIGS. 1A-1B are schematic representations of an exemplary peptide triazole conjugate of the invention and exemplary other R groups. FIG. 1A depicts HNG-156. The peptide component is SEQ ID NO. 16. The 1,2,3-triazole attached to proline 6 is 4-substituted with ferrocene. FIG. 1B depict the R groups of HNG-113, HNG-124, HNG-125 and HNG-137.

FIG. 3A is a schematic representation of HNG-156 covalently linked to a C-terminal Cys extended linker, forming HNG-156C. FIG. 3B is a graph of sensorgrams depicting direct binding of YU2 gp120 to surface-immobilized HNG-156C. The concentration of gp120 ranged from 1 to 200 nM.

FIGS. 4A and 4B are a series of graphs related to the dual antagonism of HNG-156. FIG. 4A is a graph depicting inhibition by HNG-156 of binding of YU2 gp120 to CD4. The CD4 was immobilized on a CM5 biosensor chip. 100 nM of YU2 gp120 was passed over the surface with increasing concentrations of HNG-156 from 10 to 600 nM. FIG. 4B is a graph depicting inhibition by HNG-156 of binding of YU2 gp120 to 17b by HNC-156. 17b was immobilized on a CM5 biosensor chip. 100 nM of YU2 gp120 was passed over the surface with increasing concentrations of HNG-156 from 10 to 600 nM.

FIG. 6A is a bar graph relating to inhibition of binding by HNG-156 of YU2 gp120 to IgG b6, IgG b12, or IgG F105 in the presence of CD4. The percent (%) binding of gp120 to immobilized antibodies is plotted against the concentration of HNG-156 (in nM). FIG. 6B is another bar graph of HNG-156 inhibition of gp120 binding to F105, b12, sCD4 and 17b. CD4 bs antibodies: b6, b12 and F105. CD4i antibody: 17b.

FIGS. 9A and 9B are a series of tables summarizing additional peptide triazole conjugates prepared and characterized. FIG. 9A is a table of peptide triazole conjugates described in Experimental Example 8. $IC_{50}$ (viral) was evaluated using a pseudotype virus cell infection assay. FIG. 9B is a table of peptide trizaole conjugates described in Experimental Examples 9. The proline residue in each peptide was 1,2,3-triazole modified (Azp), which was 4-substituted with ferrocene. "Cit" refers to citrulline. "$W^D$" refers to D-tryptophan.

FIG. 11A depicts SPR-analyzed effects of HNG-156, UM10 and UM12 on the sCD4 and mAb 17b interactions with HIV-1$_{YU-2}$ gp120 via SPR. Under the conditions of the experiment, the $IC_{50}$ of each compound for sCD4 was determined to be 112 nM for HNG-156, 500 nM for UM12, and no $IC_{50}$ value could be calculated for UM10. FIG. 11B depicts a graph of dose response curves for HNG-156, UM10 and UM 12, determined from the effect on HIV-1$_{YU-2}$ gp120 interaction with sCD4 and mAb 17b via ELISA. Lines between individual data points are drawn by hand to illustrate the progression of data and are not representative curve fits. All data in FIGS. 11A and 11B were obtained from represents a minimum of three repeat assays. HNG-156 data: sCD4 (■) and mAB 17b (▼), UM10 data: sCD4 (♦) and mAB 17b (●), UM12 data: sCD4 (▲) and mAB 17b (◄).

FIG. 12A depicts data for HNG-156. FIG. 12B depicts data for UM24. FIG. 12C depicts data for UM21. FIG. 12D depicts data for UM17. Samples were tested at concentrations of 2, 4, 8, 10, 50, 100, 250 and 500 nM. Black lines are experimental data and light gray lines are fits to a 1:1 Langmuir binding model with a parameter included for mass transport.

FIGS. 13A and 13B depict the structures of UM24 and UM 17, respectively. FIG. 13C is a bar graph of inhibition by UM 17 of the binding of CD4i antibodies to immobilized YU-2 gp120. The (%) of binding of antibodies mAb F105 and IgG b12 to immobilized YU-2 gp120 is plotted against the concentration of the inhibitor peptide. UM17 inhibited the binding of HIV-1 YU-2 gp120 to F105 and b12 at $IC_{50}$ values of 0.6±0.05 and 4.0±0.17, respectively.

FIG. 14A depicts data for HNG-156. FIG. 14B depicts data for UM24. FIG. 14C depicts data for UM17. FIG. 14D depicts data for UM41. Data was obtained as 25° C. in PBS, pH 7.4. Experiments in FIGS. 14A and 14B were carried out using a VP-ITC, where 2 µM gp120 in the calorimetric cell (~1.4 mL) was titrated with 10 µL aliquots of peptide at concentration of 30 µM. Experiments in FIGS. 13C and 14D were carried out using an ITC200, where 4 µM gp120 in the calorimetric cell (~200 µL) was titrated with 1.4 µL aliquots of peptides UM17 and UM41 at 50 and 100 µM respectively.

DETAILED DESCRIPTION OF THE INVENTION

Figure 1A:
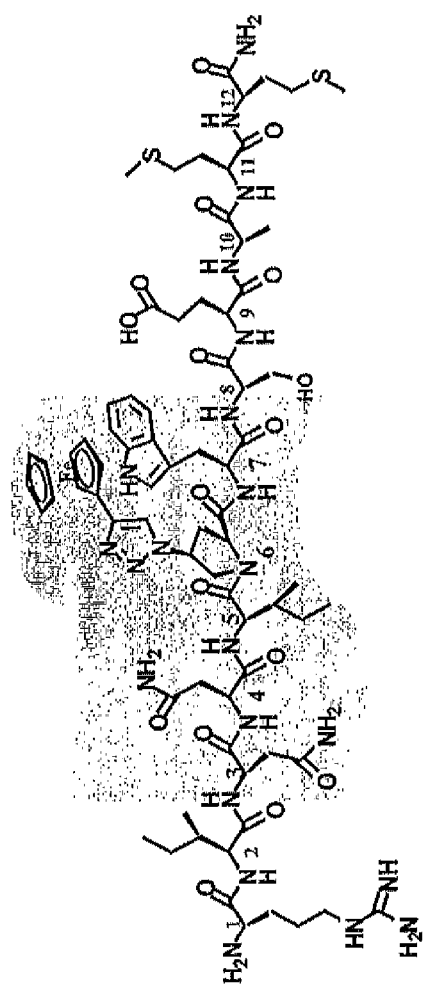

The invention springs in part from the discovery that conjugating bulky aromatic groups to a 1,2,3-triazole-modified proline residue of a peptide inhibitor of HIV-1 fusion increases the inhibitory activity, compared to the unconjugated peptide triazole. Specifically, the peptide triazole conjugates bind to HIV glycoprotein gp120 with high affinity and have potent dual antagonism of binding to CD4 and CCR5. Furthermore, in some embodiments, the peptide triazole conjugates unexpectedly have synergistic activity with another fusion inhibitor, cyanovirin-N, that binds gp120.

Thus, the invention provides a novel peptide triazole conjugate that inhibits binding of gp120 to CD4. Methods of the peptide triazole conjugate's use, including the therapeutic and prophylactic treatment of HIV-1, are also provided.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well known and commonly employed in the art.

The techniques and procedures for recombinant manipulations, including nucleic acid and peptide synthesis, are generally performed according to conventional methods in the art and various general references (e.g., Sambrook et al, 2001, Molecular Cloning, A Laboratory Approach, Cold Spring Harbor Laboratory Press, Cold Spring Harbor, N.Y.; Ausubel et al., eds, 2005, Current Protocols in Molecular Biology, John Wiley & Sons, New York, N.Y.; and Gerhardt et al., eds., 1994, Methods for General and Molecular Bacteriology, American Society for Microbiology, Washington, D.C.), which are provided throughout this document.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

The term "about" will be understood by persons of ordinary skill in the art and will vary to some extent on the context in which it is used.

"Treating," as used herein, means ameliorating the effects of, or delaying, halting or reversing the progress of a disease or disorder. The word encompasses reducing the severity of a symptom of a disease or disorder and/or the frequency of a symptom of a disease or disorder.

A "prophylactic" treatment is a treatment administered to a subject who does not exhibit signs of a disease or disorder or exhibits only early signs of the disease or disorder for the purpose of decreasing the risk of developing pathology associated with the disease or disorder.

A "therapeutic" treatment is a treatment administered to a subject who exhibits signs of pathology of a disease or disorder for the purpose of diminishing or eliminating those signs.

As used herein, "therapeutically effective amount" refers to a nontoxic but sufficient amount of an agent to provide the desired biological result. The desired biological result in some instance can be a prophylactic and/or therapeutic treatment. That result can be reduction and/or alleviation of the signs, symptoms, or causes of a disease or disorder, or any other desired alteration of a biological system. An appropriate therapeutic amount in any individual case may be determined by one of ordinary skill in the art using routine experimentation.

"Pharmaceutically acceptable carrier" refers herein to a composition suitable for delivering an active pharmaceutical ingredient (API) to a subject without excessive toxicity or other complications while maintaining the biological activity of the API. Protein-stabilizing excipients, such as mannitol, sucrose, polysorbate-80 and phosphate buffers, are typically found in such carriers, although the carriers should not be construed as being limited only to these compounds.

As used herein, the term "physiologically acceptable" ester or salt means an ester or salt form of an active ingredient in a pharmaceutical composition which is compatible with any other ingredients of the pharmaceutical composition and which is not deleterious to the subject to which the composition is to be administered.

"Polypeptide" refers to a polymer composed of amino acid residues, related naturally-occurring, structural variants, and synthetic, non-naturally-occurring analogs thereof linked via peptide bonds. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

The term "substantially pure" describes a compound, e.g., a protein or polypeptide, which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis or HPLC analysis. A compound, e.g., a protein, is also substantially purified when it is essentially free of naturally associated components or when it is separated from the native contaminants which accompany it in its natural state.

By the term "applicator," as the term is used herein, is meant any device including, but not limited to, a hypodermic syringe, a pipette, and the like, for administering the compounds and compositions of the invention.

"Instructional material," as that term is used herein, includes a publication, a recording, a diagram, or any other medium of expression, which can be used to communicate the usefulness of the composition and/or compound of the invention in a kit. The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

"Specifically bind" as used herein refers to the higher affinity of a binding molecule for a target molecule compared to the binding molecule's affinity for non-target molecules. A binding molecule that specifically binds a target molecule does not substantially recognize or bind non-target molecules.

The term "antibody," as used herein, refers to an immunoglobulin molecule which is able to specifically bind to a specific epitope on an antigen, Antibodies can be intact immunoglobulins derived from natural sources or from recombinant sources and can be immunoreactive portions of intact immunoglobulins. The antibodies in the present invention may exist in a variety of forms including, for example, polyclonal antibodies, monoclonal antibodies, intracellular antibodies ("intrabodies"), Fv, Fab and F(ab)$_2$, as well as single chain antibodies (scFv), heavy chain antibodies, such as camelid antibodies, and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

As used herein, the term "heavy chain antibody" or "heavy chain antibodies" comprises immunoglobulin molecules derived from camelid species, either by immunization with a peptide and subsequent isolation of sera, or by the cloning and expression of nucleic acid sequences encoding such antibodies. The term "heavy chain antibody" or "heavy chain antibodies" further encompasses immunoglobulin molecules isolated from an animal with heavy chain disease, or prepared by the cloning and expression of $V_H$ (variable heavy chain immunoglobulin) genes from an animal.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, an “immunoassay” refers to any binding assay that uses an antibody capable of binding specifically to a target molecule to detect and quantify the target molecule.

As used herein, “conjugated peptide” refers to a peptide having one or more modified amino acids, such as γ-azidoproline, that introduce one or more functional groups useful for conjugation. The phrase also includes such modified peptides that have been conjugated to a compound.

As used herein, “metallocene” refers to an organometallic chemical compound with the general formula $(C_5R_5)_2M$ consisting of two cyclopentadienyl rings bound on opposite sides of a central transition metal atom, M, and two cyclopentadienyl ligands coordinated in a sandwich structure, i.e., the two cyclopentadienyl anions are co-planar with equal bond lengths and strengths.

Abbreviations for amino acids, as used herein are: glycine (0), alanine (A); valine (V), isoleucine (I), leucine (L); aspartic acid (D), glutamic acid (E); asparagine (N), glutamine (Q); serine (S), threonine (T); lysine (K), arginine (R); phenylalanine (F), tyrosine (Y); tryptophan (W); cysteine (C); histidine (H); methionine (M); proline (P); and citrulline (Cit).

It is understood that any and all whole or partial increments between any numerical ranges set forth herein are included herein.

Description

I. Compounds of the Invention

Provided are peptide triazole conjugates that are antagonists of the binding reaction between HIV-1 envelope glycoprotein gp120 and CD4. Without wishing to be bound by theory, it is believed that the peptide triazole conjugates are noncompetitive allosteric antagonists of the binding between gp120 and CD4. Antagonizing binding between gp120 and CD4 subsequently antagonizes the conformational change in the trimeric gp120 that allows gp120 to interact with a chemokine receptor (e.g., CCR5 or CXCR4). These steps lead to a fusion-active state that is crucial to the HIV infection process. Accordingly, the peptide triazole conjugates are useful for treating HIV-1 by reducing or precluding the fusion of HIV-1 viral particles to T-cells and thereby reducing or precluding HIV infection. Similarly, the peptide triazole conjugates are useful for reducing the risk of HIV infection in an individual at risk of HIV-1 exposure.

In preferred embodiments, the peptide triazole conjugates also inhibit binding of gp120 and CCR5, or 17b. 17b is a monoclonal antibody that recognizes an epitope that overlaps the CCR5 binding site of gp120 and is therefore considered in the art as a CCR5 surrogate. Inhibition of binding of 17b therefore is expected to correspond to inhibition of binding to CCR5. Accordingly, in preferred embodiments, the peptide triazole conjugates of the invention are dual antagonists that inhibit gp120 binding to both CD4 and CCR5.

The peptide triazole conjugate comprises a peptide component that comprises the core sequence NIPW (SEQ ID NO. 1), wherein the proline (residue 3 of SEQ ID NO. 1) is modified according to Formula I:

Formula I 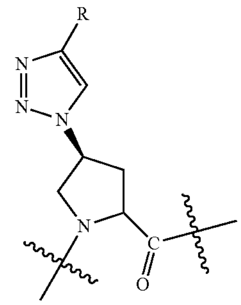 where R is a bulky aromatic group, excluding the R groups listed in Table 2 of Gopi et al., (2006, ChemMedChem 1:54-57). The excluded groups include phenyl, meta- and ortho-substituted phenyl, biphenyl, methyl-phenyl, ethyl-phenyl, 1-napthyl, 2-phenyl-ethyl. In an embodiment, R is selected from a naphthyl group; a para-alkyl-substituted phenyl, wherein the alkyl is methyl or ethyl; 2-phenylethyl; and a metallocene. The naphthyl may be substituted or unsubstituted. Preferably, R is a metallocene. A metallocene is an organometallic chemical compound with the general formula $(C_5R_5)_2M$ consisting of two cyclopentadienyl rings bound on opposite sides of a central transition metal atom, M. Exemplary transitional metals in the metallocene group are the 40 chemical elements 21 to 30, 39 to 48, 71 to 80, and 103 to 112 of the periodic table. In a preferred embodiment, the metallocene is ferrocene, $Fe(C_5H_5)_2$(bis($\eta^5$-cyclopentadienyl)iron (II)).

In some embodiments of the peptide triazole conjugate, the peptide component consists of or comprises $X_1X_2X_3$NIPW$X_4$ (SEQ ID No. 3). In some aspects, $X_1$ of SEQ ID No. 3 is selected from R and E. In these aspects, $X_2$ is preferably T and $X_3$ is preferably N. In some aspects, $X_1$ is absent and $X_2$ of SEQ ID No. 3 is selected from I, F, K, E, R and Cit. In these aspects, $X_3$ is preferably N. In some aspects, both $X_1$ and $X_2$ (i.e., $X_1X_2$) are absent, and $X_3$ of SEQ ID No. 3 is selected from N and I. When present, $X_4$ of SEQ ID No. 3 is S or T. Preferably, $X_4$ of SEQ ID No. 3 is S. In some embodiments of the peptide triazole conjugate, the peptide component consists of or comprises $X_3$NIPW (SEQ ID No. 2). In some aspects, $X_3$ of SEQ ID No. 2 is either N or I. It can readily be seen that SEQ ID No. 2. is an aspect of SEQ ID No. 3, wherein $X_1X_2$ and $X_4$ are absent. In this aspect, $X_3$ is preferably N.

Exemplary embodiments regarding the peptide component of the peptide triazole conjugate are set forth in Table 1.

TABLE 1

| SEQ ID No. | Peptide | Sample comprising peptide |
|---|---|---|
| 3 | XXXNIPWX | n/a |
| 4 | INNIPWS | UM21 |
| 5 | RINNIPWS | UM11 |
| 6 | EINNIPWS | UM13 |
| 7 | RINNIPW | UM12 |
| 8 | RNNIPWS | UM22 |

TABLE 1-continued

| SEQ ID No. | Peptide | Sample comprising peptide |
|---|---|---|
| 9 | ENNIPWS | UM23 |
| 10 | CitNNIPWS | UM24 |
| 11 | KNNIPWS | UM27 |
| 12 | FNNIPWS | UM28 |
| 13 | INNIPW | UM15 |
| 14 | NNIPWS | UM31 |
| 15 | INIPWS | UM35 |
| 21 | NNIPW | UM17 |
| 16 | RINNIPWSEAMM | HNG-156 |

In a preferred embodiment, the invention is drawn to a peptide triazole conjugate consisting essentially of SEQ ID NO. 21, wherein the proline is modified according to Formula I:

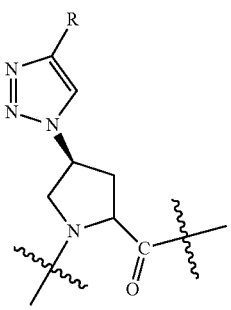

Formula I and R is a metallocene (called herein "UM17"). As demonstrated herein, UM17 has dual antagonism function, inhibiting gp120 binding to both host cell receptors (CD4 and CCR5). UM17 also exhibits substantial antiviral activity and gp120 binding.

In an embodiment, the invention is drawn to a peptide triazole conjugate comprising the sequence INNIPWS (SEQ ID NO. 4) as the peptide component, wherein the proline (residue 5 of SEQ ID NO. 4) is modified according to Formula I:

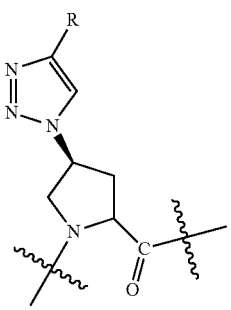

Formula I

In these embodiments, the peptide component comprising SEQ ID NO. 4 with the 1,2,3-triazol-modified proline as described herein comprises flanking residues on the N-terminus, the C-terminus, or both. Preferably, the peptide component comprises no more than about 50 residues, more preferably no more than about 30 residues, and more preferably still, no more than about 12 residues. In one embodiment, the peptide component consists essentially of SEQ ID No. 5. In an exemplary embodiment, the R is a ferrocene. This conjugate is referred herein as "UM11." In another embodiment, the peptide component consists essentially of SEQ ID No. 6. In an exemplary embodiment, the R is a ferrocene; this conjugate is referred herein as "UM13."

In an embodiment, the peptide component of the peptide triazole conjugate of the invention consists essentially of SEQ ID NO. 4. In an embodiment, R is ferrocene; this conjugate is referred herein as "UM21." UM21 has dual antagonism function, inhibiting gp120 binding to both host cell receptors (CD4 and CCR5).

In an embodiment, the peptide component of the peptide triazole conjugate of the invention consists essentially of SEQ ID No. 10. In an embodiment, R is ferrocene; this conjugate is referred herein as "UM24." UM24 is a variant of UM21 wherein the initial isoleucine of SEQ ID No. 4 is replaced with citrulline. UM24 has a high affinity ($K_d$ about 21 nM as measured by SPR) for HIV-1 YU2 gp120 envelop protein. UM24 also exhibits dual antagonism to CD4 and CCR5.

In an embodiment, the peptide component of the peptide triazole conjugate comprises or consists essentially of a sequence selected from the group consisting of SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID NO. 16, and SEQ ID NO. 21. In another embodiment, the peptide component of the peptide triazole conjugate comprises or consists essentially of a sequence selected from the group consisting of SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, and SEQ ID NO. 21. In both of these embodiments, the R group of the 1,2,3-triazole modified proline residue is preferably a metallocene, preferably ferrocene. As shown herein, exemplary peptide conjugates exhibit dual antagonism to CD4 and CCR5, as well as antiviral activity.

In an embodiment, the peptide triazole conjugate comprises RINNIPWSEAMM ("12p1"; SEQ ID NO. 16) as the peptide component, wherein proline 6 is modified with a 4-substituted 1,2,3-triazole as described. R may be a substituted or substituted naphthyl; a para-alkyl-substituted phenyl, wherein the alkyl is methyl or ethyl; 2-phenylethyl; or a metallocene. In one embodiment, R is an unsubstituted naphthyl and the peptide component consists essentially of SEQ ID NO. 16; this conjugate is referred to herein as "HNG-125" (see FIG. 1B). In one embodiment, R is a para-alkyl-substituted phenyl, and the peptide component consists essentially of SEQ ID NO. 16. The conjugate wherein the alkyl group is a methyl is referred herein as "HNG-113" (see FIG. 1B). The conjugate wherein the alkyl group is an ethyl is referred herein as "HNG-124" (see FIG. 1B). The conjugate wherein R is 2-phenylethyl is referred herein as "HNG-137" (see FIG. 1B). In preferred embodiments, R is a metallocene and more preferably, is ferrocene. In one embodiment, the peptide component consists essentially of SEQ ID NO, 16. Preferably, in this embodiment, R is ferrocene; this conjugate is referred to herein as "HNG-156" (see FIG. 1A).

As shown herein, HNG-156 has a high affinity ($K_d$ about 7.4 nM as measured by SPR) for HIV-1 YU2 gp120 envelope protein and similarly high affinity for gp120 from two other HIV-1 strains. Furthermore, HNG-156 affinity has broad specificity for diverse subtypes and clades of HIV-1. HNG-156 has dual antagonism function, inhibiting gp120 binding to both host cell receptors (CD4 and CCR5). The inhibition exhibited is consistent with a non-competitive allosteric mode of action. The high affinity of HNG-156 for gp120 enables its use as part of a solid phase chromatographic medium useful for broad-specificity affinity chromatographic purification of HIV-1 or gp120 thereof, from diverse subtypes and clades of virus.

Like HNG-156, HNG-113, HNG-124, HNG-125 and HNG-137 also have dual antagonism function. The affinity of HNG-113 for HIV-1 YU2 gp120 is about 12 nM. The affinity of HNG-124 for HIV-1 YU2 gp120 is about 9 nM. The affinity of HNG-125 for HIV-1 YU2 gp120 is about 54 nM. The affinity of HNG-137 for HIV-1 YU2 gp120 is about 13 nM. The high affinities of these peptide triazole conjugates also supports their use in affinity purification of HIV-1 or gp120 therefrom.

The invention also encompasses analogs of the peptide triazole conjugates of the invention. Analogs can differ from peptides by conservative amino acid sequence differences or by modifications which do not affect sequence, or by both.

For example, conservative amino acid changes may be made, which although they alter the primary sequence of the peptide, do not normally alter its function, Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine. Preferably, the modifications do not significantly impair the inhibition activity of the peptide triazole conjugate.

In addition to the data provided herein, information regarding the structure and function of the peptide component (e.g., SEQ ID NO. 4) is available to guide the skilled artisan in preparing peptide triazole conjugate analogs and derivatives useful in the methods of the present invention is available in the art. For instance, the Pro-Trp sequence has been identified as very important to the inhibition activity of the peptides (Ferrer et al, 1999, J Viol. 73; 5795-5802). The effects of various substitutions and truncations of SEQ ID NO. 16 have also been studied (Bjorn et al., 2004, Biochem. 43:1928-1938). Thus, the skilled artisan has guidance to preparing analogs and derivatives which will retain inhibitory function.

Derivatives of the peptide component also include multiple triazoles at different positions of the peptide, for example, at both the proline and the tryptophan of the PW sequence.

The invention also encompasses peptide triazole conjugates, which have been modified using ordinary synthetic chemical techniques so as to improve their resistance to proteolytic degradation or to optimize solubility properties or to render them more suitable as a therapeutic agent, Analogs of such polypeptides include those containing residues other than naturally-occurring L-amino acids, e.g., D-amino acids or non-naturally occurring synthetic amino acids. The peptides of the invention are not limited to products of any of the specific exemplary processes listed herein. The peptides of the invention may further be conjugated to non-amino acid moieties that are useful in their therapeutic application. In particular, moieties that improve the stability, biological half-life, water solubility, and immunologic characteristics of the peptide are useful. A non-limiting example of such a moiety is polyethylene glycol (PEG).

Covalent attachment of biologically active compounds to water-soluble polymers is one method for alteration and control of biodistribution, pharmacokinetics, and often, toxicity for these compounds (Duncan et al., 1984, Adv. Polym. Sci. 57:53-101), Many water-soluble polymers have been used to achieve these effects, such as poly(sialic acid), dextran, poly(N-(2-hydroxypropyl)methacrylamide) (PHPMA), poly(N-vinylpyrrolidone) (PVP), poly(vinyl alcohol) (PVA), poly(ethylene glycol-co-propylene glycol), poly(N-acryloyl morpholine (PAcM), and poly(ethylene glycol) (PEG) (Powell, 1980, Polyethylene glycol. In R. L. Davidson (Ed.) Handbook of Water Soluble Gums and Resins, McGraw-Hill, New York, chapter 18). PEG possesses an ideal set of properties: very low toxicity (Pang, 1993, J. Am, Coll. Toxicol. 12: 429-456), excellent solubility in aqueous solution (Powell, supra), and low immunogenicity and antigenicity (Dreborg et al., 1990, Crit. Rev. Ther. Drug Carrier Syst. 6: 315-365). PEG-conjugated or "PEGylated" polypeptide therapeutics, containing single or multiple chains of polyethylene glycol on the polypeptide, have been described in the scientific literature (Clark et al., 1996, J. Biol. Chem. 271: 21969-21977; Hershfield, 1997, Biochemistry and immunology of poly(ethylene glycol)-modified adenosine deaminase (PEG-ADA). In J. M. Harris and S. Zalipsky (Eds) Poly(ethylene glycol): Chemistry and Biological Applications, American Chemical Society, Washington, D.C., p 145-154; Olson et al., 1997, Preparation and characterization of poly(ethylene glycol)ylated human growth hormone antagonist. In J. M. Harris and S. Zalipsky (Eds) Poly(ethylene glycol): Chemistry and Biological Applications, American Chemical Society, Washington, D.C., p 170-181).

It will be appreciated, of course, that the peptides may incorporate amino acid residues which are modified without affecting activity. For example, the termini may be derivatized to include blocking groups, i.e., chemical substituents suitable to protect and/or stabilize the N- and C-termini from "undesirable degradation," a term meant to encompass any type of enzymatic, chemical or biochemical breakdown of the compound at its termini which is likely to affect the function of the compound, i.e., sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. De-carboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield de-amidated and de-carboxylated forms thereof without affect on peptide activity.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tartaric, citric, benzoic, cinnamic, mandelic, methanesulfonic, ethanesulfonic, p-toluenesulfonic, salicyclic and the like, to provide a water soluble salt of the peptide is suitable for use in the invention.

As shown herein, peptides of the invention synergize strongly with cyanovirin-N in inhibiting HIV-1 infection. Accordingly, the invention provides a pharmaceutical composition comprising a peptide triazole conjugate of the invention and cyanovirin-N (CV-N), or a functional derivative thereof. CV-N binds to gp120 and inhibits HIV infection. An exemplary amino acid sequence for cyanovirin-N is SEQ ID NO. 17. An exemplary coding sequence for cyanovirin-N is SEQ ID NO, 18.

In an embodiment, the peptide triazole conjugate is linked to cyanovirin-N. Linking may be either covalent or high affinity non-covalent linkage. Cyanovirin-N derivatives, such as a PEGylated CV-N, are useful in the invention as well, A PEGylated mutant CV-N, that retains anti-HIV activity has been reported (Zappe et al., 2008, Advanced Drug Delivery Reviews 60:79-87, Epub 16 Aug. 2007).

Covalent attachments useful in linking a peptide triazole conjugate of the invention to cyanovirin-N include, but are not limited to, standard protein cross-linking chemistries, such as glutaraldehyde activation of amine-functionalized surfaces, trialkoxy aldehyde silanes, DMP (dimethyl pimelimidate), and N-hydroxysuccinimide active ester. Non-limiting examples of high affinity non-covalent attachments include hydrophobic interactions and avidin/biotin systems.

Linking a peptide triazole conjugate to cyanovirin-N may include peptide linkers, such as glycine rich linkers, such as $Gly_4Ser$. Multiples of this sequence may also be used to optimize the synergistic activity by altering the distance and rotational freedom between the two linked entities, Peptide linkers may be incorporated into the coding sequence for cyanovirin-N or may be included in the peptide synthesis of the peptide component of the peptide triazole conjugate.

Compounds useful in conjugating a molecule with biotin include, but are not limited to, aliphatic amines, carboxylic acid, DNP-X-biocytin-X, FMOC, hydrazide, iodoacetamide, maleimide, nitriloacetic acid and succinimidyl ester, Biotin, including various spacers, linking groups and the like, and methods of biotinylation are well known to the skilled artisan. See, for example, Savage et al., 1992, Avidin-Biotin Chemistry: A Handbook, Pierce Chemical Company, Rockford, Ill.; Diamandis et al., 1991, Clin. Chem. 37:625-636; DE 3629194; U.S. Pat. Nos. 4,709,037, 4,794,082, 4,798,795, 5,180,828, and 5,252,743; and WO 85/05638, each of which is incorporated herein by reference in its entirety.

Peptide coupling chemistry may be employed to link a peptide of the invention to cyanovirin-N directly or indirectly by means of a linking agent. The standard peptide coupling chemistry methods and procedures useful in this invention are readily available. Examples of books using these methods include, but are not limited to, the following citations incorporated herein by reference: P. D. Bailey, An Introduction to Peptide Chemistry, Ed.: John Wiley & Sons, 1990; Miklos Bodansky, Peptide Chemistry, A Practical Textbook, Ed.: Springer-Verlag, 1988; Miklos Bodansky, Principles of Peptide Synthesis, "Reactivity and Structure Concepts in Organic Chemistry," Volume 16, Ed.: Springer-Verlag, 1984; and Miklos Bodansky, Principles of Peptide Synthesis, "Reactivity and Structure Concepts in Organic Chemistry," Volume 21, Ed.: Springer-Verlag, 1984. See also U.S. Pat. Nos. 4,340, 535 and 5,776,427 and EP 44167, each of which is incorporated herein by reference in its entirety.

A non-limiting example of preparing a peptide triazole conjugate of the invention linked to cyanovirin-N is as follows. A nucleic acid sequence encoding CV-N (e.g., SEQ ID NO. 18) is expressed in auxotrophic bacteria to contain a C-terminal linker with azidohomoalanine at the C-terminus. Optionally, the linker comprises one or more multiples of $Gly_4Ser$. The HNG-156 or UM24 component is synthesized to contain an N-terminal propioloyl group to enable click chemistry conjugation. The azido group on the C-terminus of CV-N and the N-terminal alkyne group on HNG-156 or UM24 will be reacted through copper-catalyzed 1,3-dipolar cycloaddition to form the triazole-linked chimeric fusion.

II. Synthesis of Peptide Triazole Conjugate

The peptides of the invention are prepared using standard methods of in vitro peptide synthesis. Examples of solid phase peptide synthesis methods include the BOC method, which utilizes tert-butyloxcarbonyl as the α-amino protecting group, and the FMOC method, which utilizes 9-fluorenylmethyloxcarbonyl to protect the α-amino of the amino acid residues, both which methods are well-known by those of skill in the art.

Exemplary methods for preparing γ-azidoproline, incorporating it into a peptide component, thereby forming a peptidyl azidoproline, and carrying out [3+2] cycloaddition with an appropriate alkyne to prepare of a peptide triazole conjugate of the invention are provided in the examples. The cycloaddition is carded out using click chemistry, which is well known in the art (Kolb et al., 2001, Angew. Chem. Int. Ed. 40:2004-2021). Appropriate alkynes to derivative the azidoproline group with a specific bulky aromatic group, such as a naphthyl or a metallocene, are apparent to the skilled artisan.

Two routes for preparing a peptidyl azidoproline are provided, but the invention is not limited to these routes of preparation. A first route includes these steps:

1. Synthesis of γ-azidoproline.
2. Solid phase peptide synthesis using either Fmoc-chemistry or Boc-chemistry; γ-azidoproline is incorporated at the appropriate position during the solid phase synthesis.
3. Click chemistry (copper catalyzed 1,3 dipolar cycloaddition) is used to conjugate on solid phase using a naphthyl, an para-alkyl-substituted phenyl or metallocene alkyne (s) and the γ-azidoproline in the peptide component.
4. Cleave resulting peptide triazole conjugate from the solid support and purification using standard methods in the art, e.g., HPLC.

In one embodiment of this route, intermediate fragment coupling is used to couple the Fmoc-Ile-Azp-OH to the C-terminal fragment of the backbone on solid phase. For instance, Fmoc-Ile-Azp-OH is coupled to residue 7 of a fragment consisting of residues 7 through 12 of SEQ ID NO. 16, or to residue 6 of a fragment consisting of residues 6 and 7 of SEQ ID NO, 4. Synthesis of Fmoc-Ile-Azp-OH is described in the examples.

A second route for the synthesis of a peptidyl azidoproline comprises total solution phase synthesis, using fragment condensation. This route includes these steps:

1. Synthesis of γ-azidoproline
2. Peptide synthesis in solution phase using fragment coupling. Fragments of the peptide component with aziodoproline are synthesized using standard peptide chemistry with necessary protecting groups for side chain protection.
3. Click chemistry (copper catalyzed 1,3 dipolar cycloaddition) is used to conjugate on solid phase using a naphthyl, an para-alkyl-substituted phenyl or metallocene alkyne (s) and the γ-azidoproline in the peptide component.
4. Removal of protecting groups using standard protocols.
5. Purification of the resulting peptide triazole conjugate using standard methods An alternative route to solution phase synthesis is to synthesize 4-substituted 1,2,3-1H-triazole-γ-substituted proline, carry out click chemistry conjugation, and use the conjugated proline in solution phase peptide synthesis. An exemplary method of preparing 4-substituted 1,2,3-1H-triazole-γ-substituted proline is provided in the examples. Use of this conjugated proline in solid phase peptide synthesis using Boc-chemistry or Fmoc-/Boc-strategy is also contemplated.

Incorporation of N- and/or C-blocking groups may also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin, so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function, e.g., with DCC, can then proceed by addition of the desired alcohol, followed by de-protection and isolation of the esterified peptide product.

Incorporation of N-terminal blocking groups may be achieved while the synthesized peptide is still attached to the resin, for instance by treatment with a suitable anhydride and nitrile. To incorporate an acetyl blocking group at the N-terminus, for instance, the resin-coupled peptide can be treated with 20% acetic anhydride in acetonitrile. The N-blocked peptide product may then be cleaved from the resin, de-protected and subsequently isolated.

The resulting peptide triazole conjugate is purified, using standard peptide purification methods known in the art such as a solid phase matrix, Non-limiting examples of such methods include chromatographic methods including column chromatography, high pressure liquid chromatography (HPLC), and thin layer chromatography. Purification using an affinity column comprising an antibody that specifically binds to the peptide triazole conjugate is also useful. Confirmation of the peptide can be achieved using standard methods, including mass spectrometry techniques, such as MALDI-TOF.

III. Methods of Use

As shown herein, the peptide triazole conjugates of the invention have a high affinity for HIV-1 gp120 envelope protein. Additionally, in preferred embodiments, they also antagonize binding to CCR5. As shown herein, a representative peptide triazole conjugate of the invention, HNG-156, inhibited infection of HIV-1 susceptible cells by fully infectious HIV-1 virus. Thus, the invention provides a method of treating HIV. The method comprises administering a therapeutically effective amount of a peptide triazole conjugate of the invention to an individual diagnosed with HIV. The invention also provides a method of reducing the risk of HIV infection. The method comprises administering a therapeutically effective amount of a peptide triazole conjugate of the invention to an individual at risk of HIV exposure. "Reducing risk" is relative to the risk that exists in the absence of the therapeutic agent.

Common methods of monitoring HIV disease status, HIV viral suppression and treatment efficacy include measuring HIV viral load and measuring $CD4^+$ T-cells. Viral load is defined as the concentration of HIV RNA in the plasma; it is usually measured as copies of the HIV genome per milliliter of plasma. Non-limiting examples of methods of measuring viral load include reverse transcription—PCR, nucleic acid sequence based amplification (NASBA) and branched DNA assay. Other measures of HIV treatment efficacy include, but not limited to, reducing or eliminating one or more symptoms of HIV, reducing the number of HIV viral infections, reducing the number of infectious viral particles, and reducing the number of virally-infected cells.

The methods of the invention may be carried out with any individual susceptible to infection by HIV or SIV. Preferably, the individual is a non-human primate, more preferably, a human.

The peptide triazole conjugate may be administered alone or in a pharmaceutical composition. The composition may further comprise other therapeutic agents. In a preferred embodiment, the composition further comprises CV-N.

The invention also provides a method of isolating viral envelope protein gp120. The method comprises contacting a solid phase matrix such as a chromatographic matrix with a sample comprising gp120, wherein a peptide triazole conjugate of the invention is linked to the matrix. Binding of gp120 to the peptide triazole conjugate linked to the matrix thus partitions the sample into a bound phase and an unbound phase. The unbound phase is then separated from the bound phase, thereby isolating gp120. Separation is typically achieved by washing the matrix and/or removing from the matrix the fluid phase comprising the unbound phase of the sample. Linkage may be covalent or non-covalent, provided the linkage has sufficiently high affinity to withstand the conditions of binding and washing the matrix. In a preferred embodiment, the peptide triazole conjugate is covalently linked to the matrix. Covalently linkages may be cleavable, reversible or irreversible. In one embodiment, the linkage is reversible. The method contemplates binding HIV-1 virus to the matrix by interaction with gp120 present on the viral particle envelope.

Peptide triazole conjugates of the invention are contemplated as lead drugs for the discovery of other therapeutics. Additionally, due to the high affinity for gp120, conjugates of the invention are useful as detection molecules, for instance, of HIV-1 viruses or gp120 therefrom. The peptides may be modified to comprises a detectable signal, such as a fluorophore, e.g., Qdot, or a chromaphore. The peptides of the invention may also serve as targeting moieties, to direct a second molecule to gp120. Examples of second molecules that may be targeted include therapeutic agents.

Thus, in yet another embodiment, a method of diagnosing an HIV infection is provided. In accordance with the method, a sample obtained from a subject (i.e., a human or animal) is assayed for the presence of gp120 by contacting the sample with a peptide triazole conjugate of the invention that has a detectable signal and detecting the signal. Detecting the signal is indicative of the presence of gp120 and is contemplated to correlate with HIV infection in the subject. Alternatively, peptide triazole conjugate bound to gp120 is detected using an antibody that specifically binds to the peptide triazole conjugate in an immunoassay. Immunoassays are disclosed elsewhere herein. The sample to be assayed can be any suitable tissue sample or fluid, but typically is blood or a blood product, such as plasma.

In preferred embodiments, the methods of the invention, including the therapeutic and prophylactic methods, are practiced with a peptide triazole conjugate wherein the peptide component is SEQ ID NO. 4 and R is a metallocene. In preferred embodiments, the metallocene is ferrocene. In another preferred embodiment, the methods are practiced using a peptide triazole conjugate wherein the peptide component is SEQ ID NO. 10 and R is a metallocene. In yet another preferred embodiment, the methods are practiced using a peptide triazole conjugate wherein the peptide component is SEQ ID NO. 16 and R is a metallocene. Preferably, the metallocene is ferrocene. In yet another preferred embodiment, the methods are practiced using a peptide triazole conjugate, wherein the peptide component is SEQ ID NO. 21 and R is a metallocene. Preferably, the metallocene is ferrocene. In yet another embodiment, the therapeutic and prophylactic methods of the invention are practiced using a pharmaceutical composition comprising a peptide triazole conjugate of the invention and cyanovirin-N or a functional derivative thereof.

IV. Administration of Pharmaceutical Compositions

The therapeutic methods of the invention encompass the use of pharmaceutical compositions comprising a peptide triazole conjugate of the invention for administration in accordance with the present invention. The pharmaceutical compositions useful for practicing the invention may be administered to deliver a dose of between about 1 ng/kg/day and about 100 mg/kg/day, and any and all whole or partial increments therebetween. In one embodiment, the invention envisions administration of a dose which results in a concentration of the compound of the present invention between about 1 µM and about 10 µM in a mammal.

Typically, dosages of peptide triazole conjugate, such as HNG-156, UM21 or UM24, which may be administered to an animal, preferably a human, range in amount from about 1 µg to about 100 g per kilogram of body weight of the animal, and any and all whole or partial increments therebetween. While the precise dosage administered will vary depending upon any number of factors, including but not limited to, the type of animal and type of disease state being treated, the age of the animal and the route of administration. Preferably, the dosage of the compound will vary from about 1 mg to about 10 g per kilogram of body weight of the animal. More preferably, the dosage will vary from about 10 mg to about 1 g per kilogram of body weight of the animal.

The pharmaceutical composition may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

Any route of administration is suitable for use in the therapeutic methods of the invention. Examples of routes of administration include oral, rectal, vaginal, parenteral, topical, pulmonary, intranasal, buccal, ophthalmic, intrathecal or another route of administration. Accordingly, pharmaceutical compositions that are useful in the methods of the invention may be prepared, packaged, or sold in formulations suitable for oral, rectal, vaginal, parenteral, topical, pulmonary, intranasal, intravenous, epidural, intraspinal, intra-arterial, buccal, ophthalmic, intrathecal, recombinant or another route of administration. Other contemplated formulations include projected nanoparticles, liposomal preparations, resealed erythrocytes containing the active ingredient, and immunologically-based formulations.

The invention encompasses the preparation and use of pharmaceutical compositions comprising a peptide triazole conjugate of the invention as an active ingredient that are useful for treatment of the diseases disclosed herein. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Such active agents include, but are not limited to, nucleoside reverse transcriptase inhibitors, non-nucleoside transcriptase inhibitors, protease inhibitors and fusion inhibitors. Nucleoside reverse transcriptase inhibitors include, but are not limited to, azidothymidine, zalcitabine, dideoxyinosine, stavudine and abacavir. Non-nucleoside transcriptase inhibitors include, but are not limited to, delavirdine, nevirapine, and efravirenz. Protease inhibitors include, but are not limited to, ritonavir), saquinivir and amprenivir. Fusion inhibitors include, but are not limited to, enfuvirtide and maraviroc. In a preferred embodiment, the peptide triazole conjugate of the invention is administered in combination with cyanovirin-N.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil, Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents, Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose, Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e. about 20° C.) and which is liquid at the rectal temperature of the subject (i.e. about 37° C. in a healthy human), Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or gel or cream or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, intracerebroventricular, surgical implant, internal surgical paint and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration, Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

In a preferred embodiment, a pharmaceutical composition comprising a peptide triazole conjugate of the invention is formulated for topical administration. In another preferred embodiment, the pharmaceutical composition comprises a peptide triazole conjugate of the invention and cyanovirin-N or a functional derivative thereof is formulated for topical administration.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient in an aqueous or oily liquid carrier. Such drops may further comprise buffering agents, salts, or one or more other of the additional ingredients described herein. Other ophthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

V. Antibodies

The invention also encompasses antibodies that specifically bind to a peptide triazole conjugate of the invention, such as HNG-156, UM21, UM24 or UM17. Such antibodies may be polyclonal or monoclonal antibodies, or functional derivatives thereof.

The generation of polyclonal antibodies is accomplished by inoculating the desired animal with the antigen and isolating antibodies which specifically bind the antigen therefrom.

Monoclonal antibodies directed against peptide may be prepared using any well known monoclonal antibody preparation procedures, such as those described, for example, in Harlow et al. (1988, In: Antibodies, A Laboratory Manual, Cold Spring Harbor, N.Y.) and in Tuszynski et al, (1988, Blood, 72:109-115). Human monoclonal antibodies may be prepared by the method described in U.S. patent publication 2003/0224490. Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, Critical Rev. in Immunol. 12(3,4):125-168) and the references cited therein. Further, the antibody of the invention may be "humanized" using the technology described in Wright et al., (supra) and in the references cited therein, and in Gu et al. (1997. Thrombosis and Hematocyst 77(4):755-759).

To generate a phage antibody library, a cDNA library is first obtained from mRNA which is isolated from cells, e.g., the hybridoma, which express the desired protein to be expressed on the phage surface, e.g., the desired antibody, cDNA copies of the mRNA are produced using reverse transcriptase, cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (2001, Molecular Cloning: A Laboratory Manual, Cold Spring Harbor Laboratory Press, Cold Spring Harbor, N.Y.).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al., (supra).

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., 1991, J. Mol. Biol. 222: 581-597. Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al., 1995, J. Mol. Biol, 248:97-105).

VI. Kits

The invention provides kit useful in the practice of the methods of the invention. In one embodiment, a kit comprising a peptide triazole conjugate of the invention and an instructional material describing how to use the conjugate to treat HIV-1 is provided. In a preferred embodiment, the conjugate is one of HNG-156, UM21, UM24 and UM17. Optionally, the kit comprises a pharmaceutical excipient, useful for preparing a pharmaceutical composition comprising the peptide triazole conjugate. In an embodiment, the kit further comprises cyanovirin-N, or derivatives thereof. Optionally, the kit comprises an applicator for administration of the conjugate.

In another embodiment, a kit useful for purifying gp120 or HIV-1 is provided. The kit comprises a peptide triazole conjugate of the invention having a linker enabling covalent attachment to a medium, such as a solid phase chromatographic medium useful in purification procedures, and an instructional material describing how to use the conjugate to purify HIV-1 or gp120 thereof. In another embodiment, the kit comprises a medium to which the conjugate.

In another embodiment, the kit comprises an antibody to a peptide triazole conjugate of the invention and an instruction material describing the use of the antibody to detect the conjugate. Optionally, the kit comprises a positive control and a negative control.

In yet another embodiment, the kit comprises a peptide triazole conjugate of the invention linked to a detectable signal and an instructional material describing its use as a detection agent for HIV-1 or gp120.

VII. Screening for Allosteric Inhibitor Candidates

As demonstrated herein, very small peptide fragments retain gp120 binding, dual antagonist activity, and antiviral activity. These data, in addition to the observation that the internal sequence cluster of triazolePro-Trp, in which triazolePro is the ferrocenyltriazole on Pro is important for function of the peptide conjugate and that the specific stereochemistry of the triazolePro-Trp cluster, suggests that the allosteric inhibitor binding site for these triazole peptide conjugates on Env gp120 involves a relative small footprint on the Env surface. While not wishing to be bound by theory, it is believed that both peptide-protein contacts and intra-peptide interactions can occur. Specifically, the triazolePro-Trp sequence provides a spatially-arranged aromatic cluster, while the N-terminal extension of residues may make hydrogen bonding interactions that help stabilize productive Env protein binding. The data suggest that the inhibitor binding site can be a viable target for small molecule inhibitors.

Consequently, the invention further provides a method for screening for a small molecule HIV-1 entry inhibitor candidate that: 1) block HNG/UM peptide binding, 2) exhibit dual antagonist activity, and 3) retain antiviral activity. In an embodiment, the method comprises identifying a small molecule that inhibits binding of a triazole peptide conjugate described herein, such as HNG-156 or UM17, to gp120 by assessing binding of the conjugate in the presence and absence of the candidate molecule. Binding can be assessed by any method known in the art, including surface plasmon resonance (SPR) interaction analyses as described herein. A small molecule that is found to inhibit binding of a conjugate is a candidate as a small molecule HIV-1 entry inhibitor. Further characterization of the small molecule can include: assessing the effect on the interaction with gp120 of sCD4 and mAB 17b and/or assessing antiviral activity, such by use of single round viral infection assays as described herein.

EXAMPLES

The invention is further described in detail by reference to the following experimental examples. These examples are provided for purposes of illustration only and are not intended to be limiting unless otherwise specified. Thus, the invention should in no way be construed as being limited to the following examples, but rather, should be construed to encompass any and all variations which become evident as a result of the teaching provided herein.

Experimental Examples 1-8

The materials and methods used in the Experimental Examples 1-8 are now described.

Virus

HIV-1 strain BaL (catalogue no. 510) was obtained from the NIH AIDS Research and Reference Reagent Program (Division of AIDS, NIAID) from Dr. Suzanne Gartner, Dr. Milculas Popovic and Dr. Robert Gallo. This strain of HIV-1, which was prepared using primary human cells of monocytic origin, uses CCR5 as its co-receptor.

Protein Reagents

HIV-1YU2 gp120 was produced as described previously in Drosophila S2 cells (Biorn et al., 2004, Biochem. 43:1928-1938; Pancera et al., 2005, J. Virol. 79:9954-9969). Cells were spun down and supernatant sterile filtered. Supernatant was purified over an F105-antibody column (NHS-activated Sepharose, Amersham; F105 antibody coupled according to manufacturer's instructions). HIV-1YU2 was eluted from the column with glycine buffer, pH 2.4, dialysed against PBS and frozen at −80° C.

sCD4 was expressed in CHO cells in a hollow fiber bioreactor. Supernatant from the hollow fiber bioreactor was purified with an SP-column (sulfopropyl substituted ion exchange column) and bound fractions were then run over a Q-column (quaternary ammonium substituted ione exchange column). Unbound material was concentrated and analysed by SDS-PAGE.

The gp120 proteins from HIV-1SF162 and HIV-192UG037-08 were used in previous inhibitor binding studies (Cocklin et al., 2007, J. Virol. 81:3645-3648); HIV-1SF162 gp120 was obtained through NIH AIDS Research and Reference Reagent Program from DAIDS and NIAID, while HIV-192UG037-08 gp120 was a gift from Dr James Arthos as reported in Cocklin et al. (2007, J. Virol. 81:3645-3648). The following monoclonal antibodies were obtained through the NIH AIDS Research and Reference Reagent Program: 2G12 from Dr Hermann Katinger; F105 from Dr Marshall Posner and Dr Lisa Cavacini; b12 from Dr Dennis Burton and Carlos Barbas and b6.

Synthesis of HNG-105 and HNG-156:

HNG-105 was prepared as described in Gopi et al (2006, ChemMedChem 1:54-57). In brief, proline 6 of 12p1 (SEQ ID NO. 16) was replaced with (2S,4S)-4-(4-phenyl-1H-1,2,3-triazol-1-yl)pyrrolidine-2-carboxylic acid. HNG-113, HNG-124, HNG-125 and HNG-137 were prepared as described in Gopi et al., (2008, J Med Chem, 51:2638-2647).

Materials used in the synthesis of HNG-156 are now described.

All Fmoc-protected amino acids, HBTU, HOBt and Hyp (OMe).HCl were purchased from Novabiochem. Fmoc-Rink amide resin was obtained from AppliedBiosystem. Solvents and other chemicals were purchased from Aldrich or Fisher and used without further purification. Peptides were synthesized on an automated peptide synthesizer (433A Applied Biosystem) at a 0.1 mmol scale. The peptides were cleaved from the resin by using a cocktail mixture of 95:2:2:1 trifluoroacetic acid/ethylenedithiol/water/thioanisole. The crude peptides were purified by using C18 column on HPLC (Beckmann Coulter) with gradient between 95:5:0.1 and 5:95:0.1 water/acetonitrile/trifluoroacetic acid. The purified peptides were confirmed by MALDI-TOF.

Synthesis of Boc-Hyp(OMs)-OMe:

Boc-L-trans-γ-hydroxyproline (2.45 g, 10 mmol) was dissolved in 50 mL of dry dichloromethane, cooled to 0° C., triethylamine (1.6 mL, 12 mmol) was added followed by methanesulfonyl chloride (0.85 mL, 11 mmol). The reaction mixture was stirred at room temperature under $N_2$ for about 8 hours and diluted with 100 mL of dichloromethane. The reaction mixture was washed with 5% HCl, 5% $Na_2CO_3$ and water. After the evaporation of organic solvent, trans-4-mesyl derivative was separated as a solid (3.1 g, 96% yield) and used directly for the next step.

Boc-L-cis-4-azidoproline:

Trans-4-mesyl proline derivative (1.61 g, 5 mmol) from the above step was dissolved in dry DMF. NaN3 (1.3 g, 20 mmol) was added. The reaction mixture was stirred overnight under $N_2$ at 70° C. The reaction mixture was poured into 50 mL of water and extracted with ethyl acetate (3×50 mL). The organic solvent was washed with water and dried over $Na_2SO_4$. After the evaporation of ethyl acetate under reduced pressure, methyl ester of Boc-L-cis-4-azidoproline separated as slightly yellowish oil (1.2 g, 90%). The methyl ester was subjected to base hydrolysis. Methyl ester of Boc-L-cis-4-azidoproline (1.08 g, 4 mmol) was dissolved in 10 mL of MeOH and 2 mL of 1N NaOH was added. The reaction mixture was stirred for 2 hours at room temperature and diluted with 50 mL of water. The MeOH was removed under reduced pressure and the aqueous layer extracted with ether (3×20 mL). The aqueous layer was acidified to pH 3 by using % 5 HCl and extracted with ethyl acetate (3×50 mL). After the aqueous work-up, the organic solvent was evaporated under reduced pressure to yield 0.97 g (95%) of Boc-L-cis-4-azidoproline.

Fmoc-L-cis-4-azidoproline:

Boc-L-cis-4-azidoproline (0.76 g, 3 mmol) was dissolved in 5 mL of dichloromethane, cooled to 0° C. 5 mL of trifluoroacetic acid was added and stirred for 30 minutes. The solvent was evaporated, the residue was dissolved in 50 mL of water and the pH was adjusted 8 by adding solid $Na_2CO_3$. Fmoc-OSu (1 g, 3 mmol) was dissolved in 10 mL of THF and added to the reaction mixture. After completion of the reaction, the reaction mixture was extracted with ether (3×50 mL). The aqueous layer was acidified to pH 2. The separated white precipitate was extracted with ethyl acetate (3×50 mL). After the aqueous work-up and evaporation of organic solvent, the yield was 0.98 g (87%) of Fmoc-L-cis-4-azidoproline. A pure sample was obtained after recrystallization from ethyl acetate/n-heptane. The pure Fmoc-L-cis-γ-azidoproline was directly used in peptide synthesis.

HNG-156 was prepared by two different routes.

Route I to HNG-156 Synthesis: Solid Phase Synthesis of HNG-156 Utilizing Intermediate Fragment Coupling of Fmoc-Ile-Azp-OH to 17-121 Fragment on Solid Phase Fragment Coupling Strategy for Synthesis of HNG-156 on a Solid Phase.

Peptide RINNI(Azp)WSEAMM (SEQ ID NO. 19; same sequence as SEQ ID No. 16 with residue 6 as azidoproline) was synthesized on the solid support. In the process of continuous synthesis, it was found that the coupling between azidoproline 6 to isoleucine 5, leads to incomplete coupling. To address this problem, triple coupling of isoleucine 5 was used and finally the unreacted imine group of azidoproline was blocked with acetic anhydride to avoid the interference of isoleucine-deleted peptide in the purification of final peptide.

In this process, the final yield of the peptide was less than expected. To address this problem, a fragment coupling strategy in solid phase peptide synthesis was utilized, Fmoc-Ile-Azp-OH was synthesized in the solution phase and coupled to free amine of Trp7 on the resin.

Synthesis of Fmoc-Ile-Azp-OH in Solution Phase.

Succinimidyl active ester of Fmoc-Ile (4.5 g, 10 mmols) was dissolved in 50 mL of DMF. Unprotected γ-azidoproline (1.87 g, 12 mmols) was dissolved in 25 mL of 20% $Na_2CO_3$ solution and added to succinimidyl ester of Fmoc-Ile. The reaction was stirred for about 12 hrs at room temperature. The reaction mixture was poured into 100 mL of water and extracted with ether (3×30 mL) to remove the unreacted Fmoc-Ile-OSu. The aqueous phase was acidified to pH 3 using 10% HCl. The liberated Fmoc-dipeptide acid was extracted to ethyl acetate (3×50 mL). The combined ethyl acetate was washed with 5% HCl, water, brine solution and passed over anhydrous $Na_2SO_4$. After the evaporation of ethyl acetate, the crude product was recrystallized using ethyl acetate and hexane. Overall yield was 4.2 g (83%). The Fmoc-dipeptide acid was directly used in the solid phase synthesis without further purification.

[3+2] Cycloaddition Reaction on Resin:

The resin of protected peptide (0.1 mmol), with L-cis-4-azidoproline group, was suspended in 5 mL of acetonitrile/water/DIEA/pyridine (4:4:1:0.5) mixture. The terminal alkyne ethynylferrocene (0.21 g, 1 mmol) was added, followed by a catalytic amount of Cu(II). The reaction was stirred overnight at room temperature over night; the solution was filtered and washed with 5% HCl, an excess of DMF and dichloromethane. HNG-156 was cleaved from the resin by using a cocktail mixture of 95:2:2:1 trifluoroacetic acidlethylenedithiol/water/thioanisole and purified by HPLC using a C-18 column. The peptide was confirmed by MALDI-TOF.

Route II to HNG-156; Total Solution Phase Synthesis

HNG-peptide conjugates were also synthesized by conventional solution-phase methods, using a fragment condensation strategy (Bodanszky, M.; Bodanszky, A. The Practice of Peptide Synthesis, 2nd. ed. Springer-Verlag, New York, 1994). The t-butyloxycarbonyl group was used as N-terminus protection, while the C-terminus was protected as a methyl ester. Intermediate deprotections were performed with 50% trifluoroacetic acid in dichloromethane and saponification (1N NaOH and methanol) for the N- and C-termini, respectively. Couplings were mediated by dicyclohexylcarbodiimide (DCC)/1-hydroxybenzotriazole (HOBt). All the coupling reactions were monitored by using TLC (thin layer chromatography). The intermediate peptides were purified by column chromatography. γ-Azidoproline (Azp) was synthesized using methyl ester of hydroxyproline (Hyp-OMe) (Gopi et al., (2006) ChemMedChem 1: 54-7).

The following peptides are subsequences of the peptide component of HNG-156 (SEQ ID NO. 19, prior to ferrocene addition to Azp), as shown in Table 2.

TABLE 2

| Subsequences | Corresponding Residues of SEQ ID No. 19 |
| --- | --- |
| Boc-Arg(Boc)2-Ile-OH | 1-2 |
| H-Asn-Asn-OMe | 3-4 |
| Boc-Arg (Boc)2-Ile-Asn-Asn-OMe | 1-4 |
| Boc-Ser(OBzl)-Glu(Bzl)-OH | 8-9 |
| H-Ala-Met-Met-OMe | 10-12 |
| Boc-Ser(OBzl)-Glu(Bzl)-Ala-Met-Met-OMe | 8-12 |
| Boc-Ile-Azp-Trp-OH | 5-7 |
| Boc-Ile-Azp-Trp-Ser(OBzl)-Glu(Bzl)-Ala-Met-Met-OMe | 5-12 |

The N-terminus dipeptide acid Boc-Arg(Boc)-2-Ile-OH was prepared by Boc-Arg (Boc)2-OSu (succinimidyl active ester). The tetrapeptide Boc-Arg (Boc)-2-Ile-Asn-Asn-OMe was prepared by [2+2] condensation, involving Boc-Arg (Boc)2-Ile-OH and H-Asn-Asn-OMe.

The pentapeptide Boc-Ser(OBzl)-Glu(Bzl)-Ala-Met-Met-OMe was prepared by [2+3] condensation involving an N-terminus dipeptide acid Boc-Ser(OBzl)-Glu(Bzl)-OH and C-terminus deprotected tripeptide H-Ala-Met-Met-OMe using DCC/HOBt. The octapeptide Boc-Ile-Azp-Trp-Ser(OBzl)-Glu(Bzl)-Ala-Met-Met-OMe was prepared by [3+5] coupling involving Boc-Ile-Azp-Trp-OH and H-Ser(OBzl)-Glu(Bzl)-Ala-Met-Met-OMe.

At the final step, the tetrapeptide acid (Boc-Arg(Boc)-2-Ile-Asn-Asn-OH) was coupled to the N-terminus deprotected octapeptide (H-Ile-Azp-Trp-Ser(OBzl)-Glu(Bzl)-Ala-Met-Met-OMe). The resulting peptidyl azidoproline (peptide with γ-azidoproline) was purified using column chromatography.

The peptidyl azidoproline was subjected to click conjugation at a preparative scale as described in the literature (Kolb et al., 2001, Angew. Chem. Int. Ed. 40: 2004-2021). The peptide was dissolved in 1:1 tert-butanol) water, ethynylferrocene was added followed by 5 mol % of $CuSO4.5H2O$ and sodium ascorbate. The final peptide was subjected to hydrozenolysis using Pd/C in methanol for the removal of benzyl groups. Finally the Boc-groups were removed by using 2M HCl in dioxane. The final peptide triazole conjugate was purified using preparative HPLC.

Alternatively, 4-substituted 1,2,3-1H-triazole-γ-substituted proline was synthesized in solution starting from methyl ester of Boc-protected-cis-γ-substituted praline using the above described protocol. After the click conjugation, the product was extracted into ethyl acetate. The click conjugated praline methyl ester was purified by column chromatography using ethyl acetate/hexane (35/65) solvent mixture. The purified product was subjected to saponification. The click conjugated Boc-protected proline was used in the above described solution phase peptide synthesis. This product may also useful in the Boc-chemistry based solid phase peptide synthesis. Further, to obtain Fmoc-protected 4-substituted-1,2,3-1H-triazolyl-proline derivative, which is useful for solid phase peptide synthesis in Fmoc-/Boc-strategy, the Boc-group of the click conjugated praline was deprotected and protected again with an Fmoc-group using Fmoc-OSu. The final product was isolated and used in the peptide synthesis.

Surface Plasmon Resonance (SPR) Kinetics Interaction Analysis:

All surface plasmon resonance experiments (SPR) were performed on a BIA3000 optical biosensor (Biocore, Inc., Uppsala, Sweden). A CM5 sensor chip was derivatized by amine coupling by using EDC.HCl/HOSu with either YU2 gp120, SF162 gp120, 92Ugo37-08 gp120, soluble CD4, mAb 17b Fab, IgG b6, IgG b12, IgG F105 or, as a control, 2B6R Fab. For direct binding experiments, YU2 gp120 was immobilized on the surface (~4000 RU); peptide analytes in PBS buffer were passed over the surface at a flow rate of 50 μL/min. with 5 minute association phase and 5 minute dissociation phase. For competition experiments, ligands (sCD4, 17b mAb, b12 and F105) were immobilized on a surface with a density of approximately 2000 RU. The indicated analytes were passed over the surfaces at a flow rate of 50 μL/minute, with 2.5 minute association phase and 2.5 minute dissociation phase. Surfaces were regenerated by using 35 mM NaOH and 1.3M NaCl for sCD4 and YU2 gp120 surfaces, and 10 mM HCl for 17b surface.

Direct binding and competition experiments for HNG-113, HNG-124, HNG-125 and HNG-137 were performed as described in Gopi et al., 2008, J Med Chem. 51:2638-2647.

Data analysis was performed using BIAEvaluation® 4.0 software (Biocore Inc., NJ). The responses of a buffer injection and responses from the control surface to which the mAb 2B6R was immobilized, were subtracted to account for non-specific binding. Experimental data were fitted to a simple 1:1 Langmuir binding model with a parameter included for mass transport. The average kinetic parameters (association [$k_a$] and dissociation [$k_d$] rates) generated front a minimum of four datasets were used to define equilibrium association ($K_A$) and dissociation constants ($K_D$).

The evaluation method for SPR inhibition data included calculation of the inhibitor concentrations at 50% of the maximal response ($IC_{50}$).

Inhibition of HIV-1 Infection Using Whole Virus Assay

P4-CCR5 MAGI cells (NIH AIDS Research and Reference Reagent Program, Division of AIDS, NAIAD) were cultured in Dulbecco's modified Eagle's media (DMEM) supplemented with 10% fetal bovine serum (FBS), sodium bicarbonate (0.05%), antibiotics (penicillin, streptomycin and kanamycin, 40 mg/mL each), and puromycin (1 mg/mL) (Charneau et al., 1994, J Mol Biol. 241:651-662), P4-CCR5 cells were seeded at a density of $1.2 \times 10^4$ cells/well in a 96-well plate approximately 18 hours prior to experiment. The cells were then incubated for 2 hours with HIV-$1_{BaL}$ (2.4 ng/mL final concentration) in the presence of HNG-156, or dextran sulphate as a positive control. After the 2 hour incubation, cells were washed, cultured for an additional 46 hours, and subsequently assayed for HIV-1 infection using the Galacto-Star1-Galactosidase Reporter Gene Assay System for Mammalian Cells as per manufacturer's instructions (Applied Biosystems, Bedford, Mass.). Infectivity remaining is expressed relative to mock-treated, HIV-1-infected cells. Data were fit to a sigmoidal inhibition model using Prism GraphPad software to yield values for $IC_{50}$, the concentration at which exposure to the compound resulted in a 50% decrease in infectivity relative to mock-treated, HIV-1-infected cells. The above assay design was similar to that used in prior studies (Krebs et al., 1999, Antiviral Res. 43:157-173).

Data for HNG-113, HNG-124, HNG-125 and HNG-137 were obtained as described in Gopi et al., 2008, J Med Chem. 51:2638-2647

In Vitro Cytotoxicity

P4-CCR5 cells were seeded at a density of $4 \times 10^4$ cells/well in a 96 well plate approximately 18 hours prior to experiment. Cells were then exposed to the indicated concentrations of HNG-156 and dextran sulphate for 2 hours. The cells were subsequently washed and assessed for viability using a 3-(4,5-dimethylthiazol-2-yl)-2,5-diphenyltetrazolium bromide (MTT) assay of viability (previously described in Krebs et al. (1999). Concentrations were tested in triplicate in two independent assays.

Data for HNG-113, HNG-124, HNG-125 and HNG-137 were obtained as described in Gopi et al., 2008, J Med Chem. 51:2638-2647

Experimental Example 1

HNG-156 Binding to HIV-1 Envelope gp120 Protein

A Biacore 3000 surface plasmon resonance (SPR) optical biosensor was used to assess the direct interactions of HNG-156 with YU2 gp120, 92UG037-08 and SF162. The real-time interactions were monitored by injecting various concentrations of HNG-156 in PBS buffer.

Figure 2:
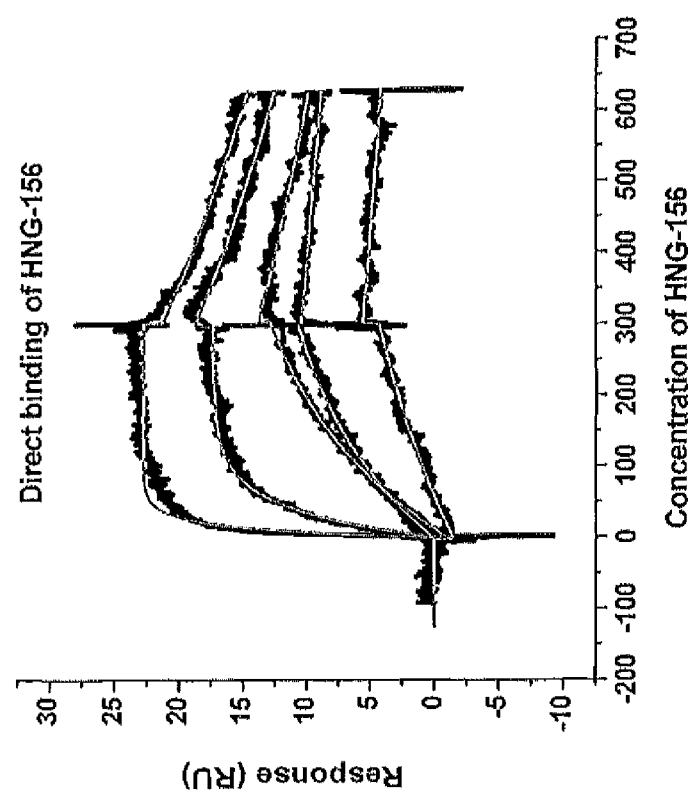
FIG. 2 is a graph of sensorgrams depicting the direct interaction of HNG-156, at varying concentrations, with immobilized gp120 (from HIV-1 strain YU-2), HNG-156 concentrations: 0, 50, 100, 250 and 500 nM.

The kinetic binding parameters and equilibrium constants for the binding of 12p1 (SEQ ID NO. 16) and peptide conjugates derived from click conjugation, HNG-105 and HNG-156, to surface-immobilized gp120 from various HIV-1 strains, determined by direct interaction SPR analysis, are given in the Table 3. Notably, HNG-156 peptide conjugate binds to the HIV-1YU-2gp120 with high affinity, KD=7.4 nM. This affinity is roughly 3-fold higher than HNG-105's affinity, and 3 orders of magnitude higher than 12p1. Direct binding results of conjugate peptide HNG-156 YU2 gp120 are shown in FIG. 2. HNG-156 showed similar potency of binding to a set diverse Glade gp120s (Clade A, Clade B and Clade C).

TABLE 3

| Peptide or Peptide Conjugate | HIV-1 env | $k_a$(1/Ms) | $k_d$(1/s) | $K_D$(M) |
|---|---|---|---|---|
| 12p1 | YU2 | $1.36 \times 10^4$ | 0.072 | $5.4 \times 10^{-6}$ |
| HNG-105 | YU2 | $3.39 \times 10^5$ | $7.79 \times 10^{-3}$ | $22.9 \times 10^{-9}$ |
|  | 92UG037-08 (A) | $1.63 \times 10^4$ | $3.0\ 10^{-2}$ | $16.3 \times 10^{-9}$ |
|  | SF162 (B) | $1.05 \times 10^5$ | $7.4 \times 10^{-3}$ | $70.5 \times 10^{-9}$ |

TABLE 3-continued

| Peptide or Peptide Conjugate | HIV-1 env | $k_a$(1/Ms) | $k_d$(1/s) | $K_D$ (M) |
|---|---|---|---|---|
| HNG-156 | YU2 | $1.29 \times 10^5$ | $9.55 \times 10^{-4}$ | $7.4 \times 10^{-9}$ |
| | 92UG037-08 (A) | $1.06 \times 10^5$ | $1.7310^{-3}$ | $16.3 \times 10^{-9}$ |
| | SF162 (B) | $1.22 \times 10^5$ | $1.110^{-3}$ | $9.0 \times 10^{-9}$ |

Binding data for other peptide triazole conjugates is provided in Table 4 (Gopi et al., 2008, J Med Chem. 51:2638-2647).

TABLE 4

| Peptide Conjugate | HIV-1 env | $k_a$(1/Ms) | $k_d$(1/s) | $K_D$ (nM) |
|---|---|---|---|---|
| HNG-105 | YU2 | $3.39 \times 10^5$ | $7.79 \times 10^{-3}$ | 23 |
| HNG-113 | YU2 | $2.4 \times 10^5$ | $2.8 \times 10^{-3}$ | 12 |
| HNG-124 | YU2 | $4.3 \times 10^5$ | $3.8 \times 10^{-3}$ | 9 |
| HNG-125 | YU2 | $1.6 \times 10^5$ | $8.6 \times 10^{-3}$ | 54 |
| HNG-137 | YU2 | $2.3 \times 10^5$ | $2.9 \times 10^{-3}$ | 13 |

Substitution at the meta- or ortho-position of the phenyl group of HNG-105 decreased affinity compared to HNG-105 (Gopi et al., 2008, J Med Chem. 51:2638-2647). In addition, polar substitutions at the para-position of phenyl also markedly decreased binding affinity. Furthermore, a peptide hiazole conjugate where R was para-butyl-phenyl had substantially no specific binding affinity at all. Thus, the discovery that para-alkyl substituted phenyl wherein the alkyl group is methyl (HNG-113) or ethyl (HNG-124) had improved affinity for YU2 gp120 was unexpected. In addition, HNG-137 (R is 2-phenylethyl) had improved affinity for YU2 gp120, compared to HNG-105.

The substituted acetylenes used for compounds in Table 4 are as follows:
  HNG-105: phenyl;
  HNG-113: p-methyl-phenyl;
  HNG-124; p-ethyl-phenyl;
  HNG-125: 1-naphthyl; and
  HNG-137; 2-phenyl-ethyl.

Experimental Example 2

Direct Binding of gp120 to Immobilized Derivative of HNG-156

Figure 3A:
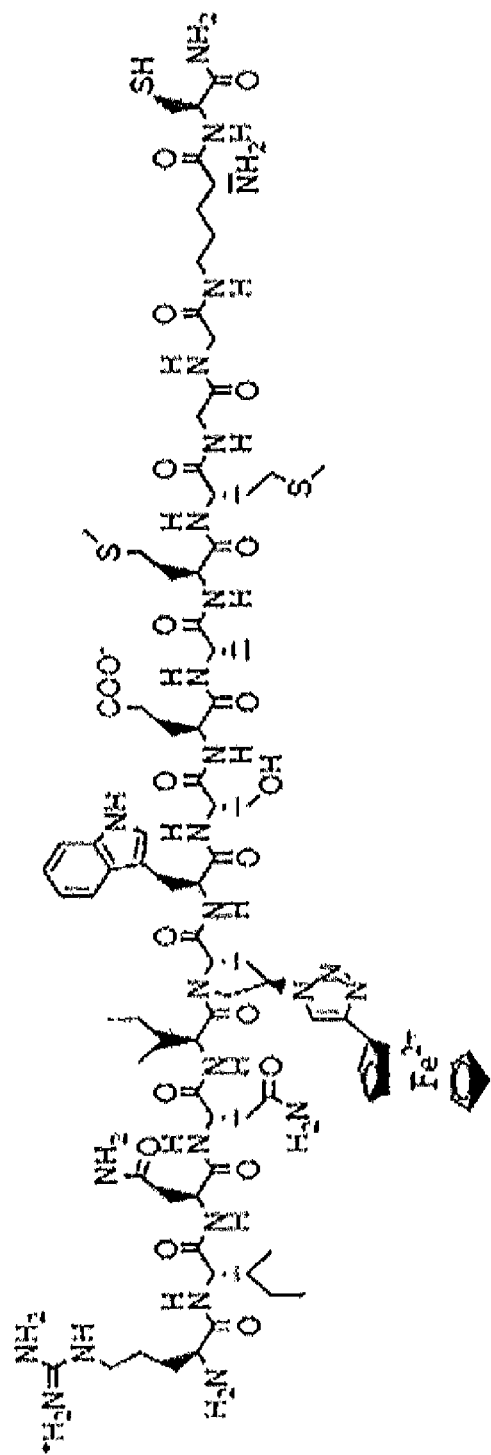
FIGS. 3A and 3B are an image and a graph related to a derivative of HNG-156.

Because HNG-156's high affinity, associated with a slow off rate, an experiment was performed to determine if gp120 could be captured on surface-immobilized HNG-156 as a route to protein purification. Different peptides were synthesized by extending the C-terminal of HNG-156, and an optimized peptide, HNG-156C, (SEQ ID NO: 20) was isolated (FIG. 3A). The sequence of HNG-156C is Arg-Ile-Asn-Asn-Ile-cPro-Trp-Ser-Glu-Ala-Met-Met-Gly-Gly-Orn($\alpha$-NH$_2$)-Cys (SH), where cPro is (2S,4S)-4-(4-ferrocenyl-1H-1,2,3-triazol-1-yl)pyrrolidine-2-carboxylic acid. The C-terminal free Cys-SH can be used to either immobilize HNG-156C on a biosensor chip or on a medium, such as chromatographic Sepharose Matrix. For this experiment, HNG-156C was immobilized on CM5 sensor chip (300 RU), using standard thiol coupling reaction. Increasing concentrations of YU2 gp120 were passed over HNG-156C, and the sensorgrams were recorded.

Figure 3B:
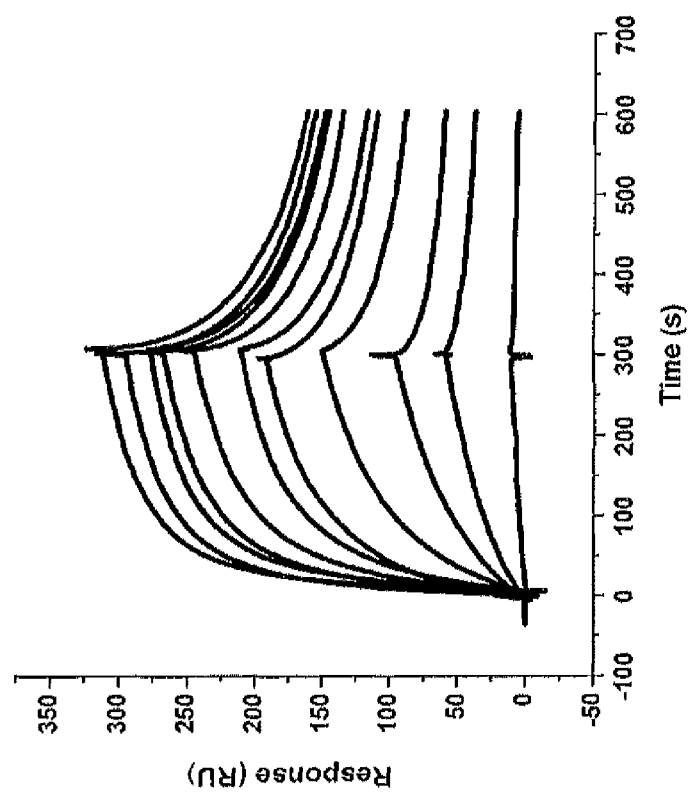

The sensorgrams of direct binding of gp120 to immobilized HNG-156C are shown in FIG. 3B. YU2 gp120 binds to immobilized HNG-156C with 5 nM affinity. This experiment demonstrates the use of HNG-156 as an immobilized ligand on a solid-phase support for affinity purification of envelope gp120.

Experimental Example 3

Dual Antagonism of CD4 and 17b Binding to YU2 gp120

The dual inhibitory effects of HNG-156 on the binding of gp120 to CD4 and 17b was measured. To assess the inhibition of binding of gp120 to sCD4 and 17b, the analyte YU2 gp120 (100 nM) was passed over immobilized sCD4, 17b and control 2B6R Fab in the absence or presence of HNG-156, with increasing concentration of HNG-156 from 10 to 600 nM, HNG-156 exhibited no direct binding to sCD4, 17b or control 2B6R.

Figure 4B:
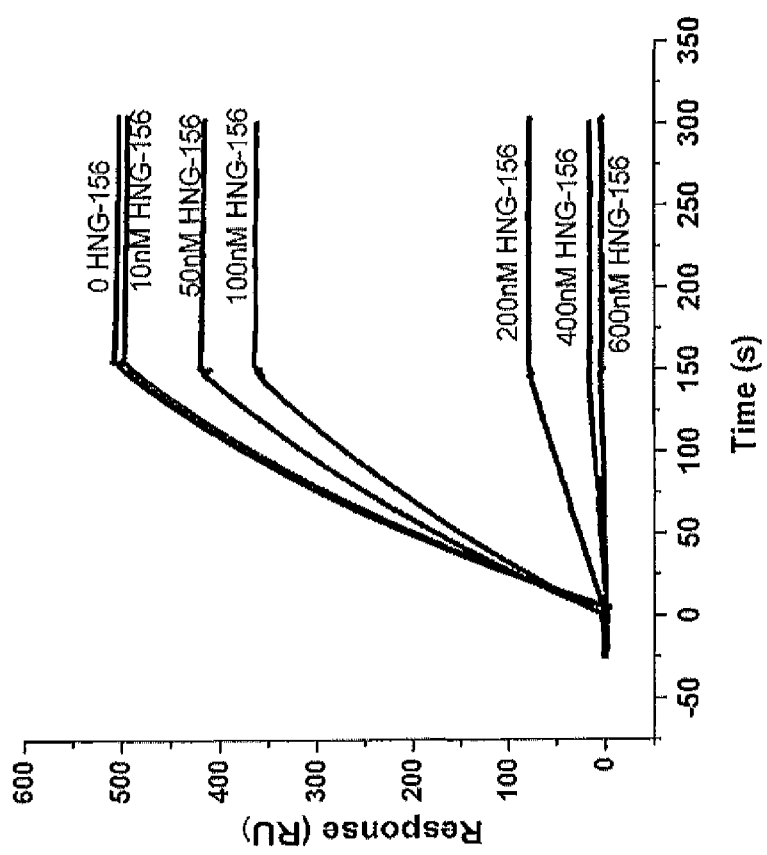

The data in FIGS. 4A and 4B illustrate that increasing the concentration of HNG-156 from 10 to 600 nM leads to complete inhibition of binding of gp120 to both sCD4 and 17b surfaces.

Experimental Example 4

Noncompetitive Binding Relationship of FNG-156 and sCD4 for gp120 as Reflected by SPR Analysis Simultaneous binding of inhibitor and ligand is h key feature distinguishing noncompetitive from competitive inhibition. To investigate whether HNG-156 and sCD4 can interact with gp120 at the same time, and thereby further validate the noncompetitive mode of inhibition by the peptide triazole conjugate, an SPR binding assay was utilized. In this assay, a high-density gp120 surface was first exposed to a saturating concentration of HNG-156 before being challenged with varying concentrations of soluble CD4 (0.007-4 $\mu$M). The control experiment without HNG-156 saturation also was performed for comparison.

Figure 5:
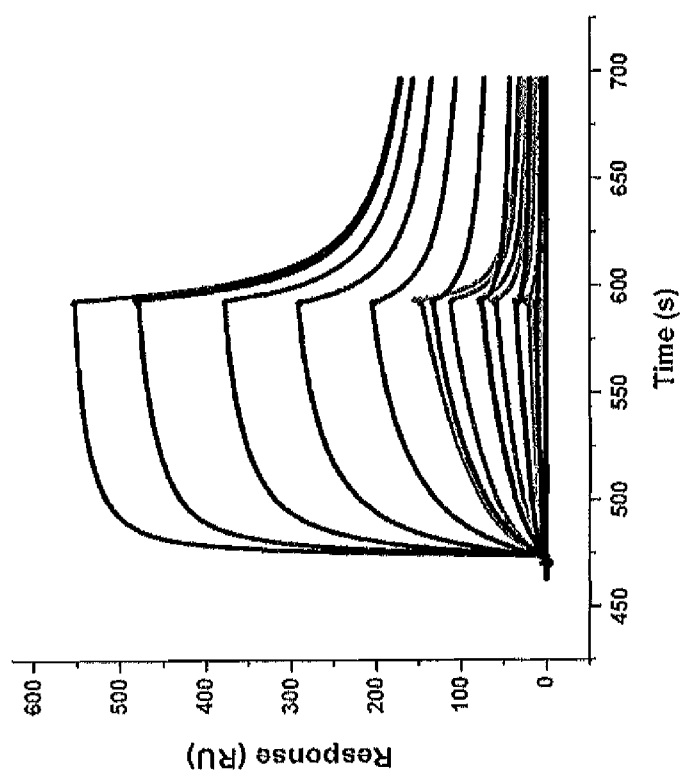
FIG. 5 is a graph of response curves of the interaction of CD4 (0.007 to 4 µM) and gp120 in the absence and in the presence of saturating concentration (15 µM) of HNG-156. The black lines are data in absence of HNG-156, while the grey are data in the presence of HNG-156.

FIG. 5 shows the resultant response curves obtained under the two different conditions. These binding curves illustrate the ability of sCD4 to bind to an HNG-156-saturated gp120 surface. The apparent equilibrium dissociation constants for sCD4 in the absence and presence of HNG-156 were approximately 13 nM and 1.7 $\mu$M respectively. In the presence of HNG-156, the affinity of CD4 was reduced by two orders of magnitude. A similar experiment with HNG-105 showed a 5-fold decrease in the affinity of CD4 (74 nM).

Experimental Example 5

Inhibition of gp120 Binding CD4 Site Antibodies (CD4 bs), and CD4-Induced Antibodies (CD4i) by HNG-156

CD4-binding site (CD4bs) antibodies recognize HIV-1 gp120 epitopes that overlap the binding site for CD4 but are believed to interact with conformations of gp120 that are distinct from that recognized by CD4 (Wyatt et al., 1998, Nature 393: 705-11; Xiang et al., 2002, J Virol 76: 9888-99). CD4 bs antibodies include both potent (e.g., IgG1b12, herein designated b12) and less potent (e.g., F105) neutralizing antibodies, CD4i antibodies recognize gp120 epitopes that overlap the chemokine receptor-binding site; these epitopes are formed and exposed after CD4 binding (Rizzuto et al., 1998, Science 280: 1949-53; Thali et al., 1993, J Virol 67: 3978-88;

Xiang et al., 2003, Virology 315: 124-34). The CD4i antibody 17b exhibits low neutralizing activity against clinical HIV-1 isolates.

In one experiment, antibodies b6, b12, or F105 were immobilized on a biosensor CM5 chip. In another experiment, antibodies F105, IgG b12, sCD4 and 17b were immobilized on a biosensor CM5 chip. In both, increasing concentrations (0-600 nM) of HNG-156 were passed over immobilized antibodies and CD4, with a constant concentration (100 nM) of YU2 gp120.

Figure 6A:
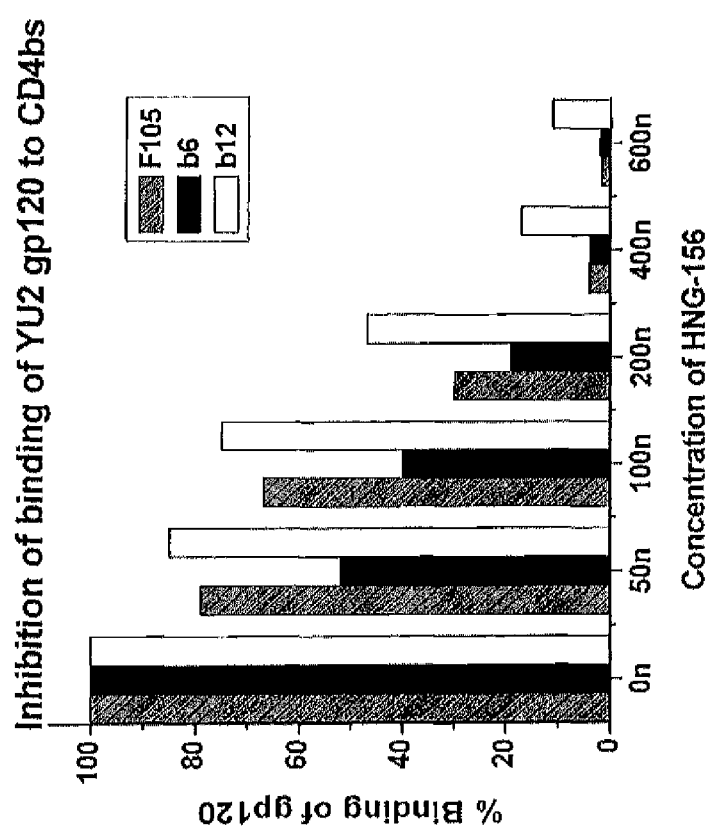
FIGS. 6A and 6B are bar graphs related to inhibition of HNG-156 to various CD4bs and CD4i antibodies and to soluble CD4.
Figure 6B:
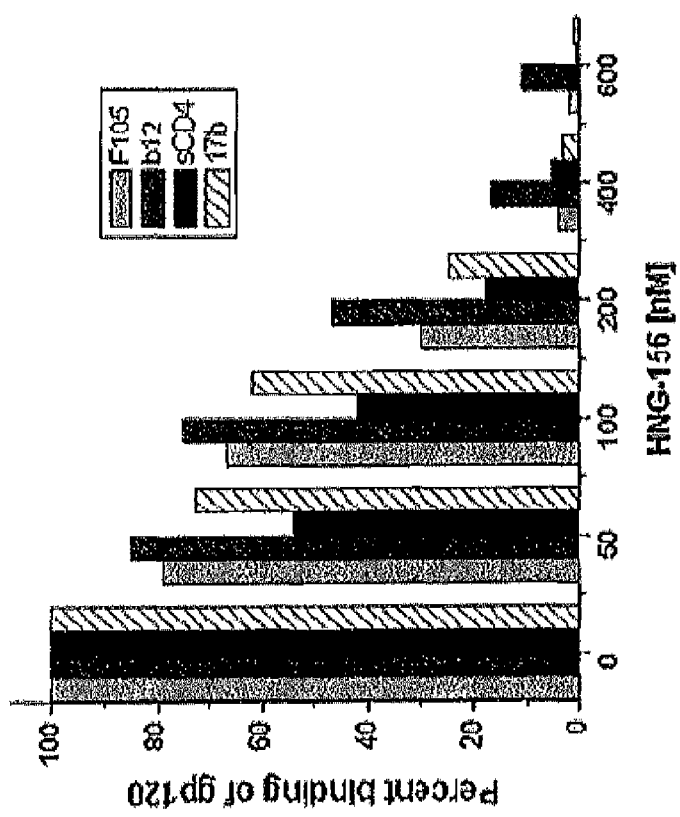

Increasing the concentration of HNG-156 suppressed gp120 binding to all of the protein ligands tested that recognize receptor and co-receptor sites. The data in FIG. 6A demonstrates the inhibition by HNG156 of binding of gp120 to mAbF105, b6 and b12. In FIG. 6B, HNG-156 inhibited binding of YU2 gp120 to F105, b12, CD4 and 17b with $IC_{50}$ values of 131 (±30), 200 (±42), 94 (±38) and 137 (±39) nM, respectively.

$IC_{50}$ data for HNG-105, HNG-113, HNG-124 and HNG-137 inhibition of gp120 binding is summarized in Table 5 (Gopi et al., 2008, J Med Chem. 51:2638-2647).

TABLE 5

| Conjugate | b6 (nM) | b12 (nM) | F105 (nM) | 17b (nM) | CD4 (nM) |
|---|---|---|---|---|---|
| HNG-105 | 106 ± 10 | 162 ± 15 | 109 ± 9 | 172 ± 42 | 154 ± 37 |
| HNG-113 | 136 ± 11 | 117 ± 13 | 76 ± 11 | 94 ± 2 | 67 ± 6 |
| HNG-124 | 235 ± 19 | 191 ± 18 | 137 ± 22 | 177 ± 42 | 146 ± 6 |
| HNG-137 | 85 ± 18 | 65 ± 14 | 23 ± 1 | 129 ± 3 | 99 ± 2 |

HNG-156 did not show any effect on the binding of another broadly neutralizing antibody, 2G12. 2G12 is a potently neutralizing and broadly reactive antibody that recognizes a cluster of oligomannose residues added post-translationally to the gp120 outer domain. 2G12 binding is independent of gp120 conformation. Thus, these data demonstrate that HNG-156 inhibits the binding of gp120 to CD4bs and CD4i antibodies.

Experimental Example 6

Inhibition of Fully-Infectious HIV-1 BaL Virus

In vitro experiments were conducted to measure the anti-HIV-1 activities of HNG-156. HNG-156, HNG-105, or dextran sulfate (DS) was incubated with subtype B strain HIV-1 BaL (R5 phenotype) and HIV-1-susceptible P4-CCR5 indicator cells for 2 hours at 37° C. P4-CCR5 indicator cells are HeLa CD4$^+$ CXCR4$^+$ CCR5$^+$ cells carrying the LacZ gene under the control of the HIV-1 long terminal repeat (LTR) promoter (Charneau et al., 1994, J Mol Biol. 241:651-662).

Figure 7:
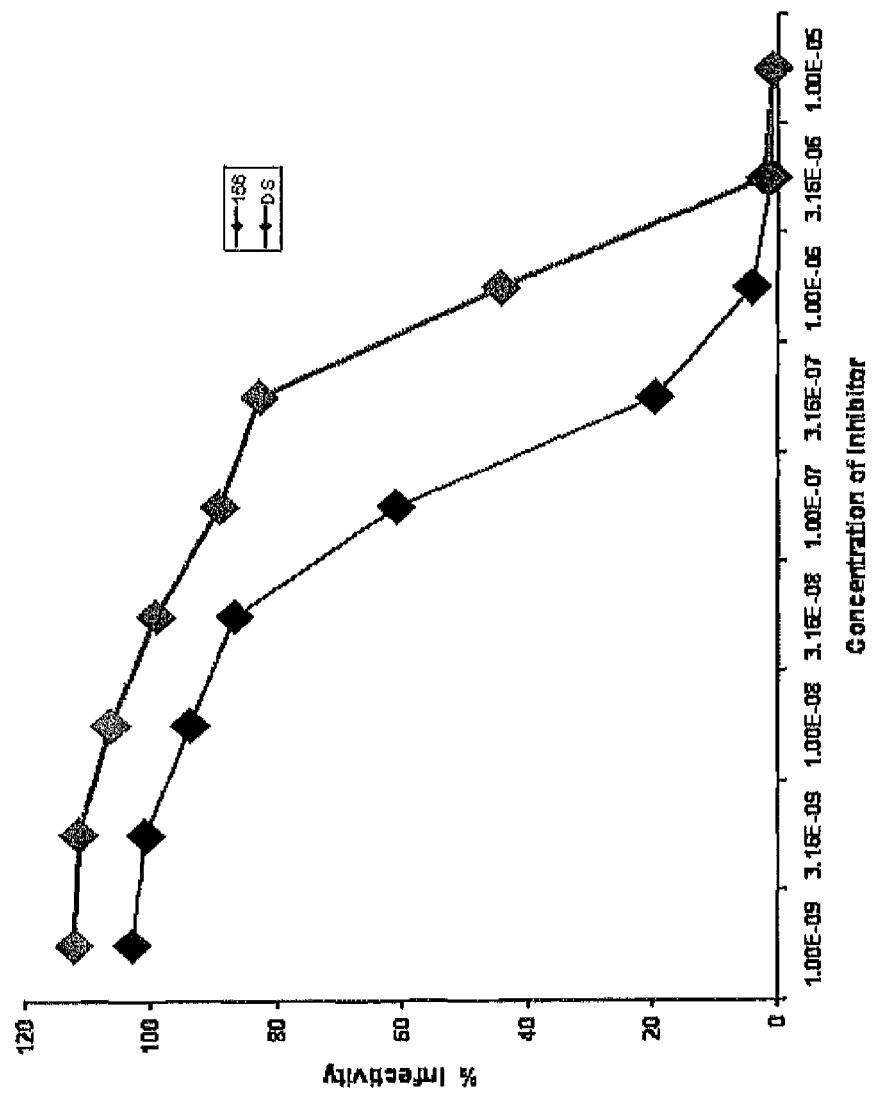
FIG. 7 is a graph depicting HNG-156 inhibition of infection of HIV-1 susceptible cells by HIV-1 strain BaL. Black diamonds are HNG-156 data. Gray diamonds are dextran sulfate data.

In an assay using HIV-1 strain BaL, HNG-156 ($IC_{50}$=96±0.1 nM; result of several independent trials) was more effective than dextran sulfate (DS; $IC_{50}$=9.8 μM or 4.9 μg/ml; result of one trial) (FIG. 7). HNG-156 was approximately 15-fold more effective than HNG-105 ($IC_{50}$=1430±100 nM) and close to three orders of magnitude more than that measured for 12p1 ($IC_{50}$=48 μM; Gopi et al., 2008, J Med Chem. 51:2638-2647 in inhibiting infection of the P4-CCR5 cells by HIV-1 strain BaL. The $IC_{50}$ values measured for HNG-113, HNG-124 and HNG-137 were 156 nM, 418 nM and 610 nM, respectively (Gopi et al., 2008, J Med Chem. 51:2638-2647), all of which are more effective than HNG-105.

HNG-156 had no effect on P4-CCR5 cell viability when assessed at concentrations as high as 0.1 mg/ml (59 mM); its $CC_{50}$ is therefore in excess of 59 mM. Similarly, HNG-113, HNG-124 and HNG-137 had no or minimal impact on cell viability at concentrations corresponding to $IC_{50}$ values.

These data indicate that the peptide triazole conjugates of the invention inhibit HIV-1 infection. HNG-156 was the most potent, with an $IC_{50}$ value of about 96 nM. Furthermore, in vitro therapeutic index (TI) estimate (calculated as the ratio of $IC_{50}$ and $CC_{50}$) for HNG-156 exceeds 600,000.

Experimental Example 7

Synergy of HNG-156 with Cyanovirin-N In Antagonizing Cell Infection by HIV-1

Cyanovirin-N (CV-N) binds specifically to the highly glycosylated viral envelope protein gp120. It has been shown to inactivate a broad range of HIV-1 strains. CV-N does not bind appreciably to the soluble form of the cellular receptor CD4 (sCD4) or to a battery of other reference proteins (Boyd et al., 1997, Antimicro Agents Chemother. 41:1521-1530).

An experiment was performed to test whether the combination of HNG-156 and CV-N was efficacious in inhibiting HIV-1 infection.

P4-CCR5 cells were incubated for 2 hours with HIV-1 strain BaL in the presence of cyanovirin alone, HNG-156 alone, or a combination of cyanovirin and HNG-156 diluted at a constant ratio of 1:8.2 by weight. Dextran sulfate (DS) was used as a comparative. After 2 hours, cells were washed, cultured for an additional 46 hours, and subsequently assayed for HIV-1 infection using the Galacto-Star β-Galactosidase Reporter Gene Assay System. Combination Indexes (CIs) were calculated using the CalcuSyn software. According to this software, developed by Chou and Talalay, CI values of <1, 1, or >1 indicate synergy, additivity, or antagonism respectively. CI values were calculated for 50, 75, and 90% HIV inhibition.

Figure 8:
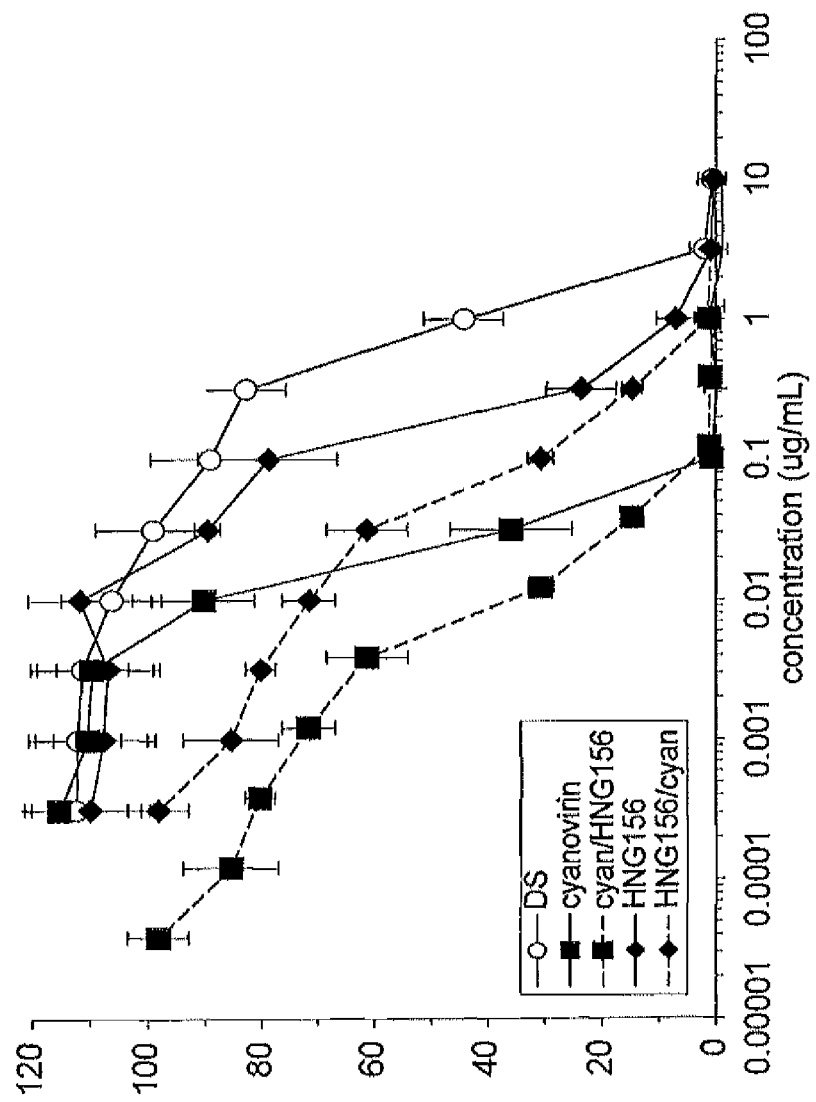
FIG. 8 is a graph depicting combination indexes (CI) values obtained in the analysis of synergy between HNG-156 and cyanovirin-N (CV-N) in inhibiting cell infection by HIV-1.

CVN and HNG-156 combinations were tested with fully infectious virus. The results observed in these experiments are shown in FIG. 8. The $IC_s$© values are tabulated in Table 6.

TABLE 6

| Viral infectivity inhibition | |
|---|---|
| Drug | $IC_{50}$ (microgram/milliliter) |
| Cyanovirin-N | 0.026 |
| HNG-156 | 0.213 |
| Cyan/HNG-156 | 0.0070 |
| HNG-156/cyan | 0.057 |
| DS | 0.900 |

In Table 6, Cyanovirin/HNG-156 refers to IC50 value obtained by plotting neutralization data as a function of CV-N concentration in the combination mixture. HNG-156/Cyanovirin refers to IC50 value obtained by plotting data as a function of HNG-156 concentration in the mixture.

Advantageously, the results show about a 10-fold improvement in the efficacy of the CV-N in viral inhibitions upon addition of HNG-156 to CVN. Furthermore, calculation of the combination indices (CI) demonstrate that the non-covalent mixture of these two agents act synergistically to inhibit HIV-1 infection. These data are summarized in Table 7. Comparison of the inhibitory effects observed with the mixture compared to the expected effect for additive effects shows that the compounds are functioning synergistically, Notably, the combination indices (CI) measured are significantly below 1, indicative of synergy. A CI of less than 0.1 is significantly less than 1 and thus indicates strong synergy. These results are also notable in comparison to HNG-113; HNG-113 does not synergize with CV-N.

TABLE 7

Combination of cyanovirin-N with HNG-156

| Drug | CI at $EC_{50}$ | CI at $EC_{75}$ | CI at $EC_{90}$ | $EC_{50}$ (µg/mL) $D_m$ |
|---|---|---|---|---|
| cyanovirin | N/A | N/A | N/A | 0.045 |
| HNG-156 | N/A | N/A | N/A | 0.450 |
| cyanovirin/HNG-156 | 0.08 | 0.13 | 0.20 | 0.002 |
| HNG-156/cyanovirin | 0.08 | 0.13 | 0.20 | 0.017 |

"EC50" = effective dose for 50% neutralization.
"EC75" = effective dose for 75% neutralization.
"EC90" = effective dose for 90% neutralization.
"Dm" = dose at which 50% neutralization occurs.

The binding sites for CVN and HNG-156 both reside within gp120 but are at sterically separate locations. It is therefore contemplated that a combination of CV-N and a peptide triazole conjugate of the invention could increase the ability to overcome resistance mutations at individual binding sites for either component alone.

Experimental Example 8

Core Peptide Sequence Analysis

The following experiment was performed to further identify the core peptide sequence for gp120 affinity, antagonism of binding to CD4 and mAB 17b, a co-receptor CCR5 surrogate, and/or antiviral activity. Accordingly, a variety of peptides, truncations of SEQ ID Nos. 4 and 16 and variants of SEQ ID No. 4 were prepared and characterized. The peptides prepared are summarized in Table 8; the table includes the consensus SEQ ID No. 3, as well as 12p1 (SEQ ID No. 16) for ease of comparison. While the peptide sequences depicted in Table 8 indicate Proline, the proline residue in each conjugate was modified to be 1,2,3-triazole 4-substituted with ferrocene,

TABLE 8

| Conjugate name | Peptide | SEQ ID No. |
|---|---|---|
| HNG-156 | RINNIPWSEAMM | 16 |
| UM10 | PWSEAMM | 19 |
| consensus | XXXNIPWX | 3 |
| UM21 | INNIPWS | 4 |
| UM11 | RINNIPWS | 5 |
| UM13 | EINNIPWS | 6 |
| UM22 | RNNIPWS | 8 |
| UM23 | ENNIPWS | 9 |
| UM24 | CitNNIPWS† | 10 |
| UM27 | KNNIPWS | 11 |
| UM28 | FNNIPWS | 12 |
| UM12 | RINNIPW | 7 |
| UM15 | INNIPW | 13 |

TABLE 8-continued

| Conjugate name | Peptide | SEQ ID No. |
|---|---|---|
| UM16 | RINNIP | 20 |
| UM31 | NNIPWS | 14 |
| UM35 | INIPWS | 15 |

†"Cit" refers to citrulline, which is an α-amino acid having the formula $H_2NC(O)NH(CH_2)_3CH(NH_2)CO_2H$.

The various peptides were prepared via solid phase synthesis. In each of these peptides, the proline residue was an azidoproline residue that was subsequently reacted with terminal alkyne ethynylferrocene as described to obtain the peptide conjugates comprising 1,2,3-triazole 4-substituted with ferrocene.

Affinity for YU2 gp120, and binding antagonism to CD4 and mAB 17b for the various peptide conjugates were assessed by surface plasmon resonance as described above.

Anti-HIV virus activity was assessed using a pseudotype virus assay as follows. Envelope-pseudotyped, luciferase-reporter viruses were produced utilizing envelope expression vectors co-transfected into 293T cells using FUGENE reagent (Fugent LLC, Madison, Wis.; commercially available from Qiagen), together with the envelope-deficient pNL4-3-$FLuc^+env^-$ provirus (catalog #3418) from Dr. Nathaniel Landau, which was obtained through the NIH AIDS Research and Reference Reagent Program, Division of AIDS, NIAID, NIH. Culture supernatants containing pseudotyped particles were collected 48-72 hours after transfection, clarified by centrifugation, aliquoted and stored at minus 80° C. until use. Pseudotype stocks were quantified using a p24 gag antigen capture ELISA (SAIC-NCI), and normalized amounts of stocks were used to infect HOS-CD4-CCR5 human osteosarcoma cells. At 48-72 hours post-infection, the cells were washed with PBS and lysed. The amount of entry mediated by each envelope was measured by detecting luciferase activity (Luciferase Assay System, Promega) with a microplate luminometer. For inhibition experiments, the pseudotype stocks were first incubated at 37° C. for 30 minutes. $IC_{50}$ values were estimated using non-linear regression analysis with Origen 7 (Northampton, Mass.). All experiments were performed at least in duplicate, and results are expressed as relative infection with respect to untreated (100%).

The affinity for YU2 gp120 of UM24 was determined to be 21 nM. The IC50 date for mAB 17b and for CD4, and the EC50 data are summarized in Table 9.

TABLE 9

| Conjugate | 17b (nM) | CD4 (nM) | $IC_{50}$ (μM) |
|---|---|---|---|
| UM10 | NA | NA | NA |
| UM21 | 161 | 86 | 7.4 ± 2.7 |
| UM11 | 168 | 85 | 10.7 ± 4.7 |
| UM13 | 154 | 79 | 3.2 ± 0.9 |
| UM22 | 181 | 123 | ND |
| UM23 | 165 | 88 | 6.6 |
| UM24 | 152 | 81 | 4.9 ± 0.8 |
| UM27 | 197 | 128 | ND |
| UM28 | 174 | 105 | 11 |
| UM12 | 218 | 124 | 12.5 ± 0.6 |

TABLE 9-continued

| Conjugate | 17b (nM) | CD4 (nM) | IC$_{50}$ (µM) |
| --- | --- | --- | --- |
| UM15 | 241 | 133 | 7.2 |
| UM16 | NA | NA | NA |
| UM31 | 16 × 10$^3$ | 5 × 10$^3$ | 10 |
| UM35 | ND | ND | 17 |

"NA" means "not active,"
"ND" means "not determined."

With the exception of UM10 or UM16, all of the peptide conjugates comprising various truncated and/or variant peptides exhibited both CD4 and mAB 17b inhibition activity (where measured) and antiviral activity (where measured). These data in the experimental example indicate that the peptides of UM11, UM12, UM13, UM15, UM21, UM22, UM23, UM 24, UM27, UM28, UM31 and UM35 are able to bind to HIV-1 gp120 believed to underlie inhibition and antiviral activities. These peptides all share the sequence NIPW, suggesting this is the minimal core sequence for HIV-1 gp120 binding. The data indicate that the amino acid residue of X in the sequence XNNIPW accepts a wide variety of residues, ranging from branched aliphatic to aromatic ring to basic and acidic side chains. This suggests that the side chain at this position may not play a direct role in binding to the HIV envelope. Three of these peptide conjugates contain a total of only 6 residues (UM15, UM31 and UM35). These data suggest that the binding site on the HIV-1 envelope protein may be relatively small. Interestingly, UM31 does not exhibit particularly high inhibition activity for CD4 and mAB 17b, however it does exhibit antiviral activity comparable to UM11 and UM28. The antiviral activity observed for UM11, UM12, UM13, UM15, UM21, UM22, UM23, UM 24, UM27, UM28, UM31 and UM35 suggest that each of these may be suitable as a therapeutic in a method of treating HIV and/or in a method of reducing the risk of HIV infection.

Experimental Example 9

The following example is an extension of Experimental Example 8, providing further characterization of the triazole peptide conjugates in Experimental Example 8, and analysis of additional embodiments.

The materials and methods used in Experimental Example 9 are now described.

Peptide Synthesis and Purification

The sequences and denotations of all peptides reported are given in Table 10 and in FIG. 9B. Peptides were synthesized manually by stepwise solid-phase synthesis. The peptide chain was assembled on the Rink amide resin (0.7 mmole/g Novabiochem, USA). All Fmoc-amino acid derivatives and coupling reagents were purchased from Chem-Impex International, Inc. (IL, USA). Synthesis grade solvents were used in all procedures. Fluorenylmethoxycarbonyl (Fmoc) group was employed for the protection of the α-amino group. Side chain protecting groups were triphenylmethyl (Trt) for Asn, tert-butyl (tBu) for Ser and tert-butyloxycarbonyl (Bac) for Trp. Coupling of each residue was carried out using HBTU/HOBt in DMF. Four equivalents of each Fmoc amino acid were used for coupling. Cleavage of the peptide from the resin was performed using 90:2.5:2.5:5(v/v) trifluoroaceticacid (TFA)/thioanisole/ethanedithiol/$H_2O$ at room temperature for 2 hours. After the filtration and washing of resin by TEA, excess of solvent was removed under vacuum. Crude peptides were treated with ice-cold diethyl ether and then centrifuged at 3000 rpm for 10 minutes at 4° C. Synthetic peptides were purified by semiPrep HPLC using a Vydac C-18 column with a 5 to 60% acetonitrile/water (0.1% TEA) gradient over 75 minutes at 3 mL/min flow rate. All peptides were purified to ≥98% homogeneity as judged by analytical reverse phase HPLC on C-18. The integrity of purified peptides was confirmed by MALDI-TOF spectra.

Protein Reagents

Production of full length HIV-1 YU-2 pg120 and soluble four domain CD4 (sCD4) was substantially as described previously for Experimental Examples 1-8.

Pseudoviral Production and Cell Infection Assays

Envelope-pseudotyped, luciferase-reporter viruses were produced utilizing envelope expression vectors (HIV-$1_{BaL}$ or VSV-G) co-transfected into 293T cells using Fugene reagent (Qiagen) together with the envelope-deficient pNL4-3-Fluc+ env− provirus (Connor et al., 1995, Virology 206(2): 935-944). Culture supernatants containing pseudotyped particles were collected 48-72 hours after transfection, clarified by centrifugation, aliquoted and stored at −80° C. until use. For inhibition experiments, the pseudotype stocks were first incubated with serial dilutions of the inhibitor at 37° C. for 30 minutes. The mixture was added to human osteosarcoma cells that stably express CD4 and CCR5 (HOS.CD4.CCR5) for 48 hours. The cells were then lysed with passive lysis buffer (Promega) followed by freeze-thaw cycles. Luciferase assays were performed using D-luciferin salt (Anaspec) as substrate and detected on a 1450 Microbeta Liquid Scintillation and Luminescence Counter (Wallac and Jet). $IC_{50}$ values were estimated using non-linear regression analysis with Origin 7 (Northampton, Mass.). All experiments were performed at least in triplicate and results were expressed as relative infection with respect to untreated (100%).

Competition ELISA

The ability of peptides to inhibit the binding of sCD4 and mAb 17b to gp120 was screened by competition ELISA. The extent of inhibition of sCD4 or mAb 17b was calculated as a percent of the uninhibited interaction. 100 ng HIV-$1_{YU-2}$gp120 in PBS buffer was coated in each well of a 96-well microtiter plate by incubating overnight at 4° C. After washing the plate three times with 200 μl/well of PBST buffer, the uncoated surface of the plates was blocked with 200 μL/well of 3% BSA in PBS for 2 hours at 25° C., followed by washing of the plate 3 times with PBST. 100 μL of sCD4 (0.1 μg/ml) was then added to each well in the presence of increasing concentration of peptide (0.01, 0.02, 0.04, 0.08, 0.16, - - - 100 μM). This and all subsequent incubation steps until detection were done in 0.5% BSA in PBS. After 1 hr incubation, the plate was washed 3 times with PBST followed by addition of 100 μL/well of biotinylated anti-CD4 antibody (eBioscience) at a 1:5000 dilution and the plate incubated for 1 hr at 25° C. After washing the plate, streptavidin-bound HRP (AnaSpec) was added at a 1:5000 dilution and again incubated for 1 hr at RT. To determine effectiveness of peptides to inhibit mAb 17b binding to gp120, 100 μL of mAb 17b (0.1 μg/ml) in the presence of increasing concentrations of peptide was added to the immobilized gp120. After 1 hr incubation at RT followed by washing three times, HRP-conjugated goat-antihuman antibody (CHEMICON) was added and incubated for 1 hour at RT. The extent of HRP conjugate binding was detected in both assays by adding 200 μL of o-phenylenediamine dihydrochloride (Sigma-Aldrich USA) reagent for 30 minutes followed by measuring OD at 450 nm using a microplate reader (Molecular Devices).

Optical Biosensor Binding Assays

Surface plasmon resonance (SPR) interaction analyses were performed on a Biacore® 3000 optical biosensor (GE). All experiments were carried out at 25° C. using standard PBS, pH 7.4, with 0.005% Surfactant P20. A CM5 sensor chip was derivatized by amine coupling by using N-ethyl-N-(3-dimethylaminopropyl)carbodimide/N-hydroxy-succinimide (Ishino et al., 2006, Biochemistry 45(4): 1106-1115) with HIV-1$_{YU-2}$ gp120 or, as a control surface, mAb 2E3 (antibody to human IL-5).

For direct binding experiments, HIV-1$_{YU-2}$ gp120 was immobilized on the sensor surface (~3500 RU); peptide analyte in PBS buffer (concentration range of 10 μM-0.61 nM) was passed over the surface at a flow rate of 50 μl min$^{-1}$ with a 5 minute association phase and a 5 minute dissociation phase. Regeneration of the surface was achieved by a one 5-second pulse of 10 mM glycine, pH 1.5. These data are summarized in Table 11.

Analysis of peptide-mediated sCD4 and mAb 17b inhibition was achieved by injecting a fixed concentration of HIV-1$_{YU-2}$ gp120 (100 nM), with increasing peptide concentrations, over a sCD4 (~2000 RU) and mAb 17b (~900 RU) surface for 5 minute association and 5 minute dissociation at a flow rate of 500 min$^{-1}$ in PBS. Regeneration of the surface was achieved by one 10-second pulse of 1.3M NaCl/35 mM NaOH and one 5-second pulse of 10 mM glycine, pH 1.5 for sCD4 and mAb 17b, respectively. These data are summarized in Table 12.

All analyses were performed in triplicate.

SPR data analyses were performed using BIAEvaluation 4.0 software (GE). The responses of buffer injection and of signals observed in a control flow cell were subtracted to account for nonspecific binding. Experimental data were fitted to a simple 1:1 binding model with a parameter included for mass transport. The average kinetic parameters (association $\{k_a\}$ and dissociation $\{k_d\}$ rates), generated from a minimum of 3 data sets, were used to define equilibrium dissociation ($K_D$) constants. The evaluation method for SPR inhibition data included a calculation of the inhibitor concentration at 50% of the maximal response (IC$_{50}$). The inhibition curve was converted into a calibration curve by the use of a fitting function. The fitting was done using the 4-parameter equation in BIAevaluation software:

$$\text{Response} = R_{high} - \frac{(R_{high} - R_{low})}{1 + \left(\frac{Conc}{A_1}\right)^{A_2}}$$

Where $R_{high}$ is the response value at high inhibitor concentrations and $R_{low}$ is response at low inhibitor concentrations. Conc is the concentration of inhibitor, and $A_1$ and $A_2$ are fitting parameters. At IC$_{50}$ the following is true:

$$\text{Response} = R_{high} - \frac{(R_{high} - R_{low})}{2}$$

Under this condition, $A_1$=Conc and is therefore taken as the desired IC$_{50}$ parameter.

Isothermal Titration Calorimetry

Isothermal titration calorimetric experiments were performed using high-precision calorimetric systems of model VP-ITC or ITC$_{20}$ from MicroCal Inc. The titrations were performed by stepwise addition of peptide to gp120 contained in the calorimetric cell at a constant temperature of 25° C. The VT-ITC has a cell volume of ~1.4 mL and the volume per injection of peptide is 10 μL where as ITC$_{20}$ has a cell volume of ~200 μL and the peptide is injected in the step of 1.4 μL. For the experiments carried out in the VP-ITC the concentration of gp120 was about 2 μM and the syringe contained the peptide at a concentration about 30 μM. For the experiment carried out using ITC$_{20}$ gp120 was prepared at about 4 μM and the peptide at 50-100 μM. The solutions contained within the calorimetric cells and injector syringes were prepared in PBS, pH 7.4 and thoroughly degassed to avoid bubble formation in the calorimetric cell. The heat evolved upon each injection of the peptide solution was obtained from the integral of the calorimetric signal. The heat associated with binding of a ligand to the protein in the cell was obtained by subtracting the heat of dilution from the heat of reaction. Heats of dilution due to mismatch between the syringe and cell solutions were negligible in all experiments. The individual heats were plotted as a function of the molar ratio, and nonlinear regression of the data provided the enthalpy change (ΔH) and the association constant ($K_a$=1/$K_d$).

The results for Experimental Example 9 are now presented.

The sequences and denotations of all peptides reported are given in Table 10.

TABLE 10

| Conjugate name | Peptide | SEQ ID No. |
|---|---|---|
| HNG-156 | RINNIPWSEAMM | 16 |
| UM10 | PWSEAMM | 19 |
| consensus | XXXNIPWX | 3 |
| UM21 | IN<u>NIPWS</u> | 4 |
| UM11 | RIN<u>NIPWS</u> | 5 |
| UM13 | EIN<u>NIPWS</u> | 6 |
| UM22 | RN<u>NIPWS</u> | 8 |
| UM23 | EN<u>NIPWS</u> | 9 |
| UM24 | CitN<u>NIPWS</u>† | 10 |
| UM27 | KN<u>NIPWS</u> | 11 |
| UM28 | FN<u>NIPWS</u> | 12 |
| UM12 | RIN<u>NIPW</u> | 7 |
| UM15 | IN<u>NIPW</u> | 13 |
| UM16 | RINNIP | 20 |
| UM17 | NNIPW | 21 |
| UM41 | NIPWS | 22 |
| UM31 | N<u>NIPWS</u> | 14 |
| UM32 | RNIPWS | 23 |
| UM33 | ENIPWS | 24 |
| UM34 | CitNIPWS† | 25 |
| UM35 | I<u>NIPWS</u> | 15 |
| UM24-DW | CitN<u>NIPW</u>$^D$S† ‡ | n/a |

†"Cit" refers to citrulline, which is an α-amino acid having the formula H$_2$NC(O)NH(CH$_2$)$_3$CH(NH$_2$)CO$_2$H,
‡ "W$^D$" refers to D-tryptophan, Binding data, including association and dissociation rates, regarding gp120 for the peptide triazole conjugates are summarized in Table 11.

TABLE 11

| Conjugate | Kd (nM) | Ka (1/Ms) | Kd (1/S) |
|---|---|---|---|
| HNG-156 | 6.9 | 5.5E+05 ± 0.5 | 3.8E−03 ± 0.1 |
| UM10 | 809 | 1.1E+03 ± 0.6 | 8.90E−04 ± 1.2 |
| UM21 | 169 | 8.3E+03 ± 8.7 | 1.4E−03 ± 0.5 |
| UM11 | 65.6 | 3.2E+05 ± 1.8 | 2.1E−02 ± 0.6 |
| UM13 | 5.5 | 5.6E+05 ± 3.2 | 3.1E−03 ± 2 |
| UM22 | 13.3 | 5.1E+05 ± 2.1 | 6.8E−03 ± 0.4 |
| UM23 | 26.2 | 1.3E+05 ± 0.2 | 3.4E−03 ± 0.2 |
| UM24 | 4.1 | 7.0E+05 ± 2.8 | 2.9E−03 ± 1.2 |
| UM27 | 14.9 | 5.9E+05 ± 1.4 | 8.8E−03 ± 2.1 |
| UM28 | 11.3 | 3.8E+05 ± 2.1 | 4.3E−03 ± 0.8 |
| UM12 | 12.9 | 1.4E+05 ± 1.3 | 1.8E−03 ± 1.3 |
| UM15 | 8.5 | 3.9E+05 ± 3.6 | 3.3E−03 ± 0.3 |
| UM16 | >10000 | Not detectable | Not detectable |
| UM17 | 333 | 1.8E+04 ± 0.67 | 6.0E−03 ± 1.25 |
| UM41 | >10000 | Not detectable | Not detectable |
| UM31 | 18.6 | 4.2E+05 ± 1.5 | 7.8E−03 ± 1.1 |
| UM32 | 939 | 3.3E+03 ± 2.7 | 3.1E−03 ± 1.5 |
| UM33 | 1636 | 1.1E+03 ± 0.9 | 1.8E−03 ± 0.8 |
| UM34 | >10000 | Not detectable | Not detectable |
| UM35 | >10000 | Not detectable | Not detectable |
| UM24-DW | >10000 | Not detectable | Not detectable |

Binding data regarding mAB 17b and sCD4, and antiviral activity data are presented in Table 12.

TABLE 12

| Conjugate | mAb 17b (nM) | sCD4 (nM) | $IC_{50}$ (µM) |
|---|---|---|---|
| HNG-156 | 152 ± 4 | 112 ± 10 | 0.8 ± 0.26 |
| UM10 | NA | NA | 35 ± 15 |
| UM21 | ND | ND | 7.4 ± 2.7 |
| UM11 | ND | ND | 4 ± 2.9 |
| UM13 | ND | ND | 1.2 ± 0.3 |
| UM22 | ND | ND | 11 ± 5 |
| UM23 | ND | ND | 5.8 ± 1.1 |
| UM24 | 138 ± 11 | 118 ± 27 | 2.6 ± 1.0 |
| UM27 | ND | ND | 23 ± 8.0 |
| UM28 | ND | ND | 13 ± 1.7 |
| UM12 | 250 ± 39 | 500 ± 306 | 6.8 ± 0.3 |
| UM15 | 238 ± 4 | 236 ± 17 | 6.9 ± 0.8 |
| UM16 | ND | ND | NA |
| UM17 | 241 ± 63 | 147 ± 6 | 33 ± 11 |
| UM41 | ND | ND | NA |
| UM31 | 172 ± 16 | 191 ± 3 | 36 ± 6.0 |
| UM32 | ND | ND | NA |
| UM33 | ND | ND | NA |
| UM34 | ND | ND | NA |
| UM35 | ND | ND | 17 ± 7 |
| UM24-DW | NA | NA | NA |

"NA" means "not active."
"ND" means "not determined."

9 I. Retention of Function of N-Terminal Fragment Containing the Central TriazolePro-Trp Cluster HNG-156 was truncated into C and N-terminal heptapeptides UM10 (residues 6-12 of SEQ ID No. 19) and UM12 (residues 1-7 of SEQ ID No. 19), such that both truncated peptides retained the central triazole-indole moiety. The two truncates were compared for their ability to bind gp120 using SPR. Increasing concentrations of UM10 and UM 12 were passed separately over a high-density (3500 RU) YU-2 gp120 surface. The binding data were fit to a bimolecular binding process. The N-terminal fragment peptide UM12 binds to gp120 with 12.9 nM Kd, while the C-terminal fragment peptide UM10 binds to gp120 with 809 nM Kd, which is 100 fold lower affinity vs 12mer peptide of HNG-156 (see Table 11).

Figure 10:
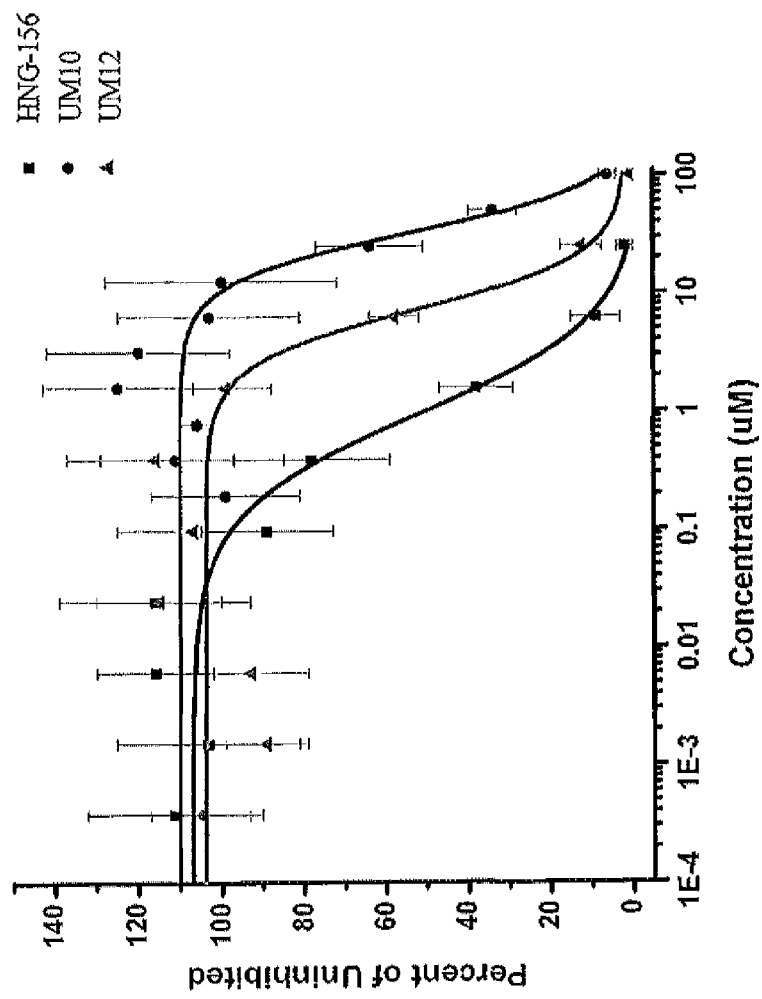
FIG. 10 depicts a graph regarding the analysis of antiviral potencies of HNG-156, UM10 and UM12, using single round viral infection assays. Pseudotyped HIV-1$_{BaL}$ was pre-incubated with serial dilutions of HNG-156, UM10 and UM12 for 30 minutes at 37° C. The virus-inhibitor mixture was then added to HOS.CD4.CCR5 for 48 hours. The amount of viral entry was determined based on luciferase activity. Data points were fit to a simple sigmoidal inhibition model using Origin software to derive the best-fit lines. The $IC_{50}$ values were 0.9 µM for HNG-156, 35 µM for UM10 and 6.8 µM for UM12. The data represent a minimum of three repeats.

The antiviral activities of UM10 and UM12 were assessed using pseudotyped HIV-1$_{BaL}$ infection of target cells. The dose response profiles of infection inhibition are shown in FIGS. 10A and 10B, and the $IC_{50}$ data from these responses are given in Table 12. UM12 was more potent than UM10 for inhibiting viral infection activity. Neither of these conjugates inhibited negative control viruses pseudotyped with the VSV-G envelope, indicating that the inhibition is specific to the HIV-1 envelope glycoprotein.

Figure 11A:
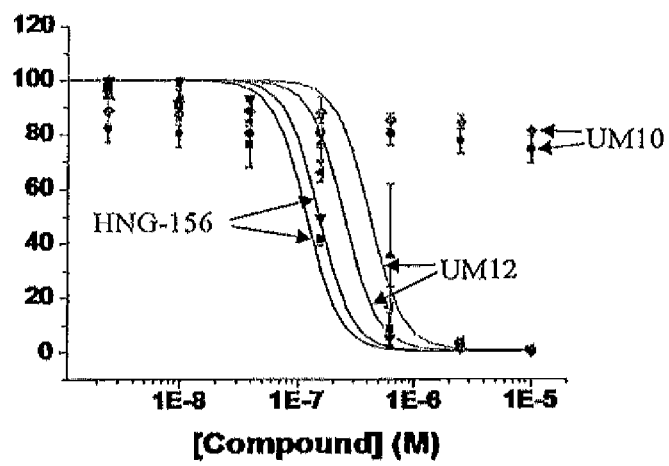
FIGS. 11A and 11B are a series of graphs relating to assessment of dual antagonism.
Figure 11B:
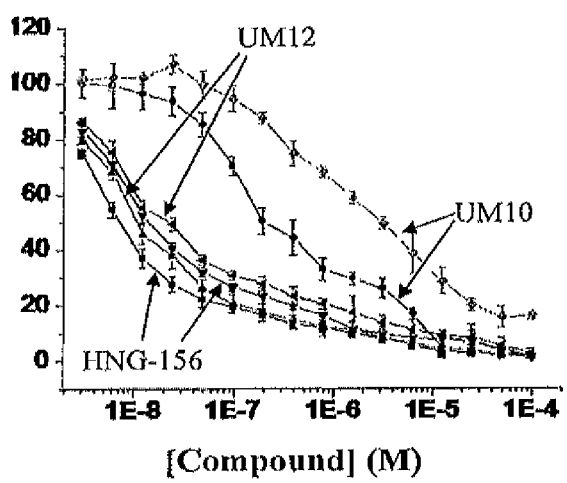

Since HNG-156 inhibits gp120 interactions at both its CD4 and co-receptor binding sites, the inhibition by UM10 and UM12 of YU-2 gp120 interactions with immobilized sCD4 and mAb 17b was examined using both ELISA and SPR analysis. As shown in FIGS. 11A and 11B, UM12 maintained the dual antagonist signature. Mean inhibitory concentration ($IC_{50}$) for UM12 was 500 nM and 250 nM for sCD4 and mAb 17b, respectively (Table 12). UM10 was unable to inhibit either sCD4 or mAb 17b binding to gp120 at concentrations up to 10 µM, in contrast to its detectable binding to gp120 and inhibition of viral entry. In control experiments, neither UM10 nor UM12 exhibited direct binding to either a sCD4 or mAb 17b SPR chip surface.

To confirm the relative lack of importance of C-terminal residues in HNG-156, the binding and dual antagonist property of peptide UM11 were evaluated, in which the additional serine residue was present at the C-terminus. Incorporation of this Ser residue led to only a fractional improvement in the direct binding and antiviral properties vs. those for UM12 (Table 12).

Figures 12A, 12B, 12C, 12D:
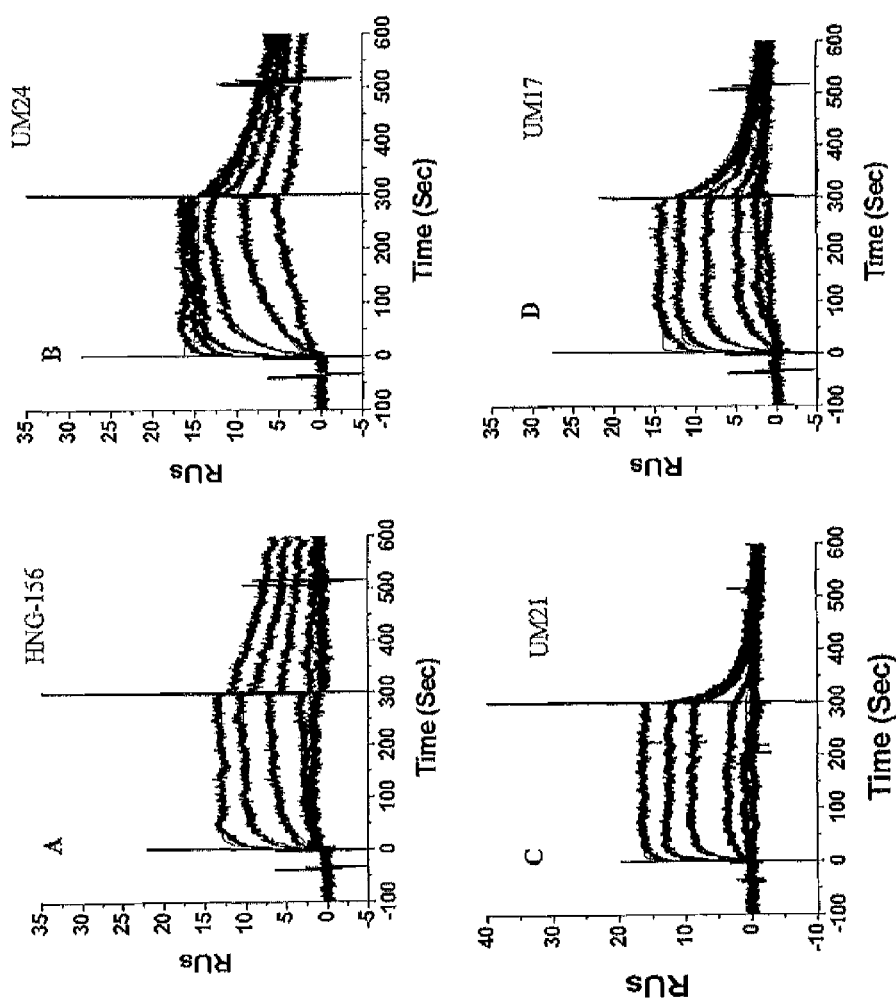
FIGS. 12A-12D are a series of graphs of sensograms for the direct binding of various peptides to immobilized YU-2 gp120.

9 II. Progressive Truncation and Sequence Variation of the N-Terminal Residues to Identify Minimum Length Active Dual Antagonist Sequences To assess the functional importance of N-terminal amino acids, the significance of Arg residue 1 for direct binding to gp120 and antiviral activity of peptide UM11 was examined by replacing this residue by negative charge residue Glu (UM13). UM13 exhibited enhanced direct binding affinity for gp120 (Kd=5.5 nM; Table 11) as well as antiviral potency ($IC_{50}$=1.2 µM) (Table 12). Although UM13 showed somewhat increased efficacy vs UM11, both Arg and Glu at position 1 were acceptable. These findings argue that the positive charge side chain of Arg residue at the N-terminal is relatively unimportant. Consistent with this result, deletion of the Arg residue (UM21) led to only partially reduced direct binding activity (Kd=169 nM), mainly due to increased off-rate of the peptide in direct binding analysis (FIG. 12C). However, UM21 retained significant antiviral potency.

Figure 13A:
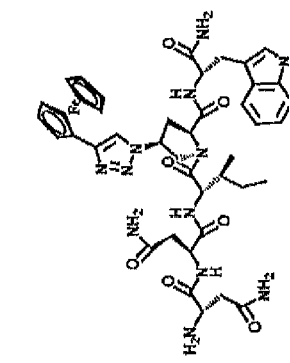
FIGS. 13A-13C depict a series of chemical structures and a graph.
Figure 13B:
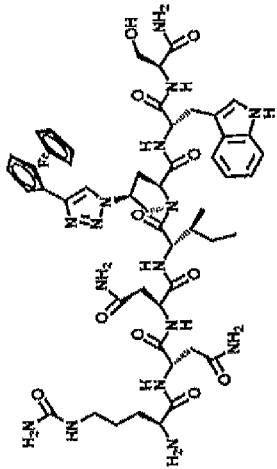
Figure 13C:
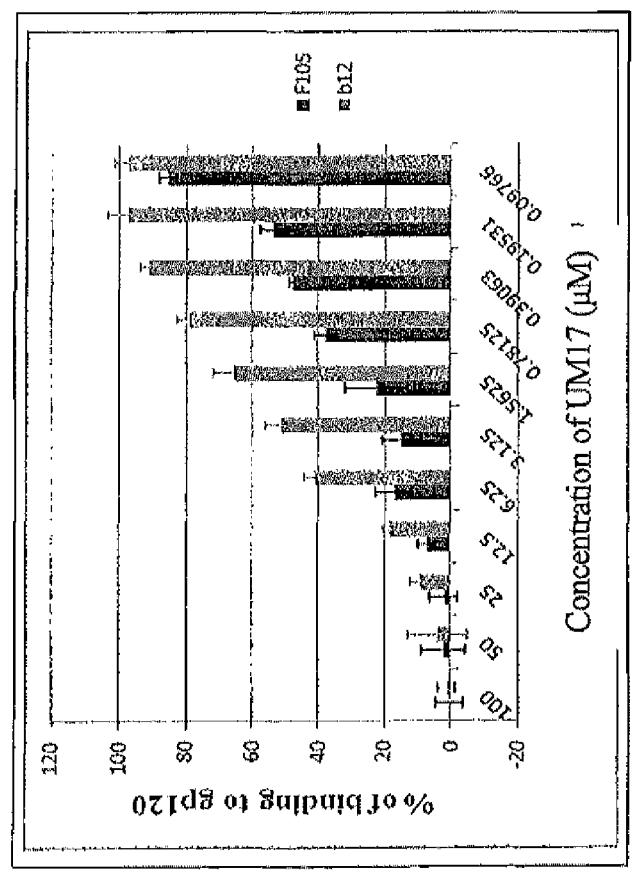
Figures 14A, 14B, 14C, 14D:
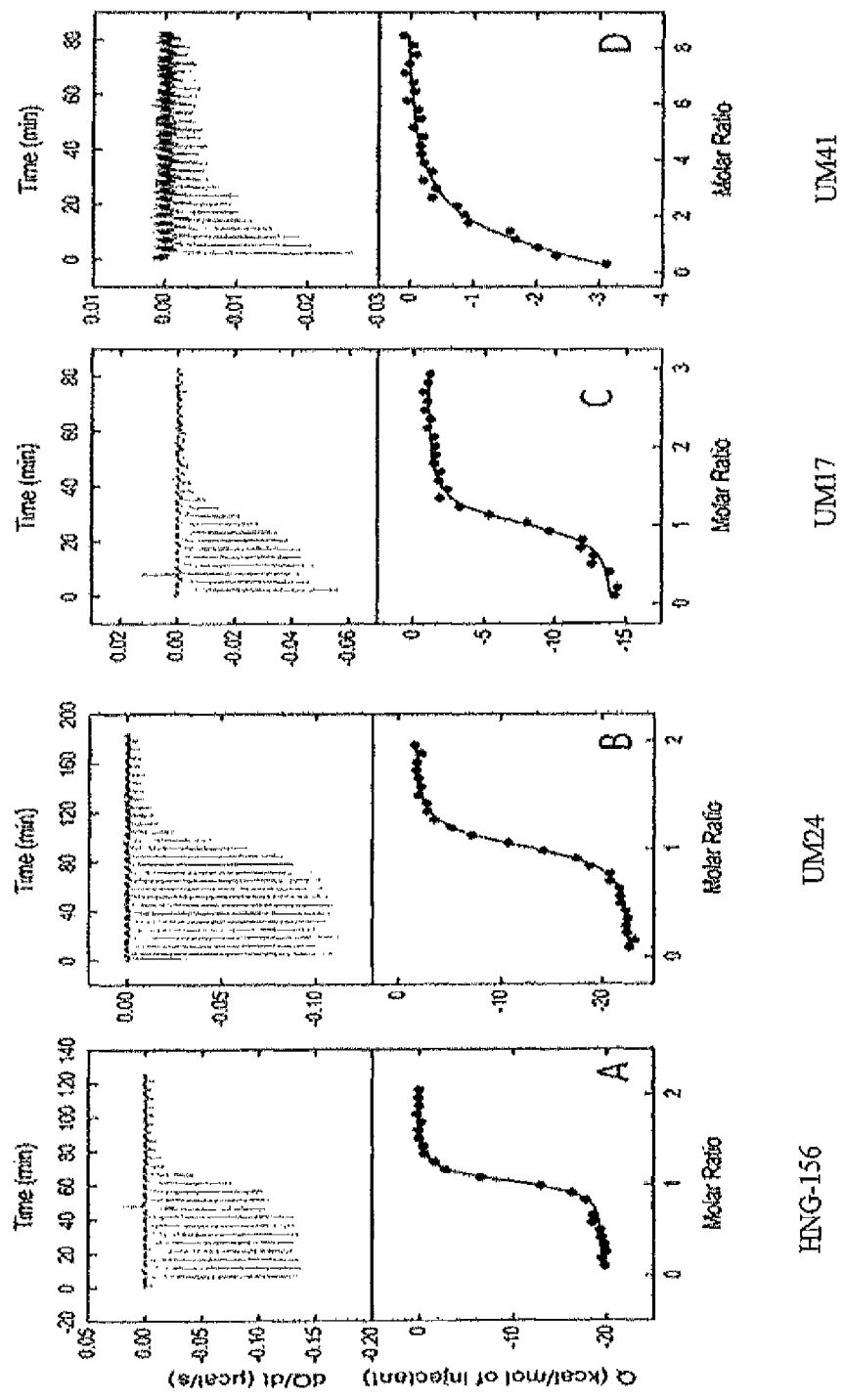
FIGS. 14A-14D are a series of graphs of calorimetric titration data of gp120 with various peptides.

To evaluate side chain variations with different functionalities of the N-terminal residue 1 in UM21, a series of heptapeptides (X-Asn-Asn-Ile-Azp-Trp-Ser; SEQ ID No. 26), where X=arginine (UM22; FIG. 13A), glutamic acid (UM23), citrulline (UM24), lysine (UM27) and phenylalanine (UM28) were evaluated for their direct binding and inhibition of viral infection activities. In general all of these led to conjugates with similar antiviral potencies and binding activities (Tables 11 and 12). Interestingly, replacement with the unnatural amino acid citrulline (UM24; FIG. 13A) significantly increased the direct binding affinity to Kd=4.1 nM (FIG. 12B; Table 11) and antiviral potency to $IC_{50}$=2.6 µM (Table 12). Variation of this amino acid side chain did not affect the direct binding nor the antiviral potency of the sevenmer peptide, indicating that specific interaction of the side chain of amino acid in the Ile position with gp120 is not essential for the viral inhibition function. This was further supported by the substantial (though reduced) activities observed with hexa peptide UM31, in which Ile residue of UM21 was truncated.

In contrast to the relatively small effects from sequence replacements at N-terminal residues of 1 and 2 of SEQ ID No. 19, residue 3 is substantially more sensitive. Replacement of the N-terminal Asn residue in UM31 with Arg (UM32), Glu (UM33), Cit (UM34) and Ile (UM35) was assessed. Side chain variations of Asn 3 were found to lead to substantial reduction of antiviral activity and direct binding affinity to gp120 (Tables 11 and 12). These data suggest that the side chain at residue 3 of SEQ ID No. 19 is important for function. This conclusion is further supported by the complete loss of activity demonstrated by penta peptide (UM41), which was derived from truncation of the N-terminal Asn residue in UM31, 9 III. Active Core Sequence within the Peptide Triazole Inhibitors Based on the above findings that several residues in the N- and C-terminal regions had limited importance for gp120 binding and inhibition, the limits of truncation of compound UM12 were explored, Deletion of the C-terminal Trp residue led to complete loss of activity in UM16. In contrast, two six-residue fragments, UM15 and UM31, were found to retain substantial binding (Table 11), dual site antagonism and antiviral activity (Table 12). A five-residue peptide (UM17; FIG. 13B), containing residues 3-7 of parent peptide HNG-156, was tested. This peptide was found by SPR to bind to gp120 with weakened though still finite affinity with Kd=333 nM (FIG. 12D) and exhibited significant antiviral activity ($IC_{50}$=33 μM). An alternative penta peptide, UM41, containing residues 4-8 of parent peptide HNG-156, was found to be inactive.

In addition to its dual antagonism of CD4 and 17b binding, the core peptide UM17 was found to suppress the interaction with other ligands of gp120 that are dependent on the conformation of the Env protein. HNG-156 inhibits binding of monoclonal antibodies mAb's b12 and mAb F105 to the viral glycoprotein gp120 (see Experimental Example 5). ELISA data depicted in FIG. 3C show that the active pharmacophore pentapeptide UM17 retains similar functionalities, 9 IV. Importance of Stereochemistry in the triazolePro-Trp Cluster The active core sequences identified herein comprise a C-terminal hydrophobic cluster. Previous work has shown that the stereochemistry of the triazolePro residue in this cluster in HNG-156 was critical; specifically, it was demonstrated that the S configuration of triazole is active, while R configuration is not (Gopi et al., 2008, J Med Chem. 51(9): 2638-2647). The stereochemical requirements in the Trp position of the cluster were therefore examined. Compared to UM24 (all-L amino acids), the activity of UM24-DW, with D-Tip substituted, was largely lost (Table 12). In sum, therefore, it is evident that the function of peptide triazole inhibitors is highly dependent on the stereochemistry of the "triazolePro-Trp" cluster.

9V. Preservation of Conformational Effects on gp120 by Truncated Peptide Triazoles.

Prior ITC analysis with analogues of HNG-156 demonstrated that binding of the parent peptide triazole had the ability to structurally constrain gp120 (Gopi et al., 2008, J Med Chem. 51(9): 2638-2647). The change in conformation induced upon binding would explain the ability of the peptide to inhibit both CD4 and coreceptor binding. Therefore, an experiment was performed to assess whether the property of conformational structuring was retained in peptide triazole truncates. The results of FIG. 14A-14D compare the calorimetric titration data for HNG-156 with those for UM24, UM17 and UM 41. The thermodynamic parameters obtained by ITC for these and other peptides are summarized in Table 13,

TABLE 13

| Peptide triazole conjugate | $K_d$ (nM) | ΔG (kcal/mol) | ΔH (kcal/mol) | −TΔS (kcal/mol) |
|---|---|---|---|---|
| HNG-156 | 7.8 | −11.1 | −19.9 | +8.8 |
| UM12 | 65 | −9.8 | −19.7 | +9.9 |
| UM24 | 25 | −10.4 | −16.7 | +6.3 |
| UM31 | 80 | −9.7 | −13.8 | +4.1 |
| UM15 | 45.5 | −10.0 | −16.6 | +6.6 |
| UM17 | 69 | −9.8 | −13.2 | +3.3 |
| UM41 | 2300 | −7.7 | −6.1 | −1.6 |

Except for low affinity UM41, all of the peptide truncates tested were similar to HNG-156 in exhibiting large favorable enthalpy and unfavorable entropy changes. CD4 binding to gp120 is also characterized by a large change in favorable enthalpy (−34.5 kcal/mol) that is coupled to a large unfavorable change in entropy (ΔS=−79 cal (K×mol); −TΔS=23.6 kcal/mol). Together with a large negative heat capacity change ($\Delta C_p$=−1800 cal/(K×mol), these features make up the thermodynamic signature for a binding event that is associated with a large conformational structuring of gp120 (Schon et al., 2006, Biochemistry 45(36): 10973-10980; Leavitt et al., 2004, Curr Protein Pept Sci 5(1): 1-8). Although the thermodynamic changes are much larger for CD4 binding to gp120, while not wishing to be bound by theory, it is believed that some conformational structuring is likely to be induced also upon binding of the peptides truncates presented here.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A peptide triazole conjugate comprising a peptide component comprising the sequence $X_1X_2X_3$NIPW$X_4$ (SEQ ID No. 3), wherein $X_1$ is absent or E, wherein $X_2$ is F, K, E, R and Cit;

wherein $X_3$ is N or I;

wherein $X_4$ is S or T;

wherein the proline in SEQ ID No. 3 is modified according to Formula I:

(Formula I)

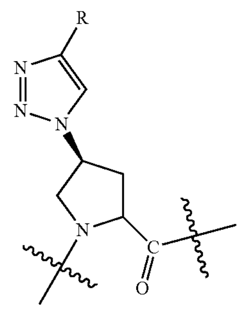

wherein R is a bulky aromatic group.

2. The peptide triazole conjugate of claim 1, wherein the bulky aromatic group is selected from the group consisting of a naphthyl group; a para-alkyl-substituted phenyl, wherein the alkyl is methyl or ethyl; 2-phenylethyl; and a metallocene.

3. The peptide triazole conjugate of claim 1, wherein the bulky aromatic group is a metallocene.

4. The peptide triazole conjugate of claim 3, wherein the metallocene is ferrocene.

5. The peptide triazole conjugate of claim 1, wherein $X_3$ is N.

6. The peptide triazole conjugate of claim 1, wherein the sequence $X_1X_2X_3$NIPW$X_4$ of the peptide triazole conjugate is a sequence selected from the group consisting of: SEQ ID No. 6, SEQ ID No. 8, SEQ ID No. 9, SEQ ID No. 10, SEQ ID No. 11, and SEQ ID No. 12.

7. A pharmaceutical composition comprising the peptide triazole conjugate of claim 1 and a pharmaceutically acceptable carrier.

8. The pharmaceutical composition of claim 7, wherein the bulky aromatic group of the peptide triazole conjugate is selected from the group consisting of a naphthyl group; a para-alkyl-substituted phenyl, wherein the alkyl is methyl or ethyl; 2-phenylethyl; and a metallocene.

9. The pharmaceutical composition of 7, wherein R of the peptide triazole conjugate is ferrocene.

10. The pharmaceutical composition of claim 7, wherein the sequence $X_1X_2X_3$NIPW$X_4$ of the peptide triazole conjugate is a sequence selected from the group consisting of: SEQ ID No. 6, SEQ ID No. 8, SEQ ID No. 9, SEQ ID No. 10, SEQ ID No. 11, and SEQ ID No. 12.

11. A pharmaceutical composition comprising the peptide triazole conjugate of claim 1, cyanovirin-N or a functional derivative thereof, and a pharmaceutically acceptable carrier.

12. The pharmaceutical composition of claim 11, wherein the bulky aromatic group of the peptide triazole conjugate is selected from the group consisting of a naphthyl group; a para-alkyl-substituted phenyl, wherein the alkyl is methyl or ethyl; 2-phenylethyl; and a metallocene.

13. The pharmaceutical composition of claim 12, wherein the peptide triazole conjugate is linked to the cyanovirin-N or a functional derivative thereof.

14. The pharmaceutical composition of claim 11, wherein the N-terminal residue of the peptide triazole conjugate is covalently linked to the C-terminal residue of the cyanovirin-N or functional derivative thereof.

15. The pharmaceutical composition of claim 11, formulated for topical or parenteral administration.

16. The pharmaceutical composition of claim 11, wherein R of the peptide triazole conjugate is ferrocene.

17. The pharmaceutical composition of claim 11, wherein the sequence $X_1X_2X_3$NIPW$X_4$ of the peptide triazole conjugate is a sequence selected from the group consisting of: SEQ ID No. 6, SEQ ID No. 8, SEQ ID No. 9, SEQ ID No. 10, SEQ ID No. 11, and SEQ ID No. 12.

18. A method of treating HIV infection in an HIV-infected individual, the method comprising administering to the individual a therapeutically effective amount of the pharmaceutical composition of claim 7.

19. The method of claim 18, wherein the bulky aromatic group of the peptide triazole conjugate is selected from the group consisting of a naphthyl group; a para-alkyl-substituted phenyl, wherein the alkyl is methyl or ethyl; 2-phenylethyl; and a metallocene.

20. The method of claim 18, wherein the bulky aromatic group of the peptide triazole conjugate is a metallocene.

21. The method of claim 20, wherein the metallocene of the peptide triazole conjugate is ferrocene.

22. The method of claim 18, wherein the pharmaceutical composition further comprises cyanovirin-N or a functional derivative thereof.

23. The method of claim 18, wherein the sequence $X_1X_2X_3$NIPW$X_4$ of the peptide triazole conjugate is a sequence selected from the group consisting of: SEQ ID No. 6, SEQ ID No. 8, SEQ ID No. 9, SEQ ID No. 10, SEQ ID No. 11, and SEQ ID No. 12.

24. A method of reducing HIV infectivity in an individual, the method comprising administering to the individual a therapeutically effective amount of the pharmaceutical composition of claim 7.

25. The method of claim 24, wherein the bulky aromatic group of the peptide triazole conjugate is selected from the group consisting of a naphthyl group; a para-alkyl-substituted phenyl, wherein the alkyl is methyl or ethyl; 2-phenylethyl; and a metallocene.

26. The method of claim 24, wherein the bulky aromatic group of the peptide triazole conjugate is a metallocene.

27. The method of claim 26, wherein the metallocene of the peptide triazole conjugate is ferrocene.

28. The method of claim 24, wherein the pharmaceutical composition further comprises cyanovirin-N or a functional derivative thereof.

29. The method of claim 24, wherein the administration is one of topical and parenteral.

30. The method of claim 24, wherein the sequence $X_1X_2X_3$NIPW$X_4$ of the peptide triazole conjugate is a sequence selected from the group consisting of: SEQ ID No. 6, SEQ ID No. 8, SEQ ID No. 9, SEQ ID No. 10, SEQ ID No. 11, and SEQ ID No. 12.

31. A method of isolating a viral envelope protein gp120 from a sample, the method comprising contacting sample comprising gp120 with the peptide triazole conjugate of claim 1 linked to a solid phase matrix, wherein:

the gp120 binds to the peptide triazole conjugate thereby partitioning the sample into a bound phase and an unbound phase; and separating the unbound phase from the bound phase, thereby isolating the gp120 from the sample.

* * * * *

SEQUENCE LISTING

```
<160> NUMBER OF SEQ ID NOS: 26

<210> SEQ ID NO 1
<211> LENGTH: 4
<212> TYPE: PRT
<213> ORGANISM: Artificial Sequence
<220> FEATURE:
<223> OTHER INFORMATION: chemically synthesized

<400> SEQUENCE: 1
```

```
Asn Ile Pro Trp
1

<210> SEQ ID NO 2
<211> LENGTH: 5
<212> TYPE: PRT
<213> ORGANISM: Artificial sequence
<220> FEATURE:
<223> OTHER INFORMATION: chemically synthesized
<220> FEATURE:
<221> NAME/KEY: misc_feature
<222> LOCATION: (1)..(1)
<223> OTHER INFORMATION: Xaa can be any naturally occurring amino acid

<400> SEQUENCE: 2

Xaa Asn Ile Pro Trp
1               5

<210> SEQ ID NO 3
<211> LENGTH: 8
<212> TYPE: PRT
<213> ORGANISM: Artificial sequence
<220> FEATURE:
<223> OTHER INFORMATION: chemically synthesized
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 3

Xaa Xaa Xaa Asn Ile Pro Trp Xaa
1               5

<210> SEQ ID NO 4
<211> LENGTH: 7
<212> TYPE: PRT
<213> ORGANISM: Artificial Sequence
<220> FEATURE:
<223> OTHER INFORMATION: chemically synthesized

<400> SEQUENCE: 4

Ile Asn Asn Ile Pro Trp Ser
1               5

<210> SEQ ID NO 5
<211> LENGTH: 8
<212> TYPE: PRT
<213> ORGANISM: Artificial sequence
<220> FEATURE:
<223> OTHER INFORMATION: chemically synthesized

<400> SEQUENCE: 5

Arg Ile Asn Asn Ile Pro Trp Ser
1               5

<210> SEQ ID NO 6
<211> LENGTH: 8
<212> TYPE: PRT
<213> ORGANISM: Artificial sequence
<220> FEATURE:
<223> OTHER INFORMATION: chemically synthesized

<400> SEQUENCE: 6

Glu Ile Asn Asn Ile Pro Trp Ser
1               5
```

```
<210> SEQ ID NO 7
<211> LENGTH: 7
<212> TYPE: PRT
<213> ORGANISM: Artificial sequence
<220> FEATURE:
<223> OTHER INFORMATION: chemically synthesized

<400> SEQUENCE: 7

Arg Ile Asn Asn Ile Pro Trp
1               5

<210> SEQ ID NO 8
<211> LENGTH: 7
<212> TYPE: PRT
<213> ORGANISM: Artificial sequence
<220> FEATURE:
<223> OTHER INFORMATION: chemically synthesized

<400> SEQUENCE: 8

Arg Asn Asn Ile Pro Trp Ser
1               5

<210> SEQ ID NO 9
<211> LENGTH: 7
<212> TYPE: PRT
<213> ORGANISM: Artificial sequence
<220> FEATURE:
<223> OTHER INFORMATION: chemically synthesized

<400> SEQUENCE: 9

Glu Asn Asn Ile Pro Trp Ser
1               5

<210> SEQ ID NO 10
<211> LENGTH: 7
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: citrulline

<400> SEQUENCE: 10

Xaa Asn Asn Ile Pro Trp Ser
1               5

<210> SEQ ID NO 11
<211> LENGTH: 7
<212> TYPE: PRT
<213> ORGANISM: Artificial sequence
<220> FEATURE:
<223> OTHER INFORMATION: chemically synthesized

<400> SEQUENCE: 11

Lys Asn Asn Ile Pro Trp Ser
1               5

<210> SEQ ID NO 12
<211> LENGTH: 7
<212> TYPE: PRT
<213> ORGANISM: Artificial sequence
<220> FEATURE:
<223> OTHER INFORMATION: chemically synthesized

<400> SEQUENCE: 12

Phe Asn Asn Ile Pro Trp Ser
```

-continued

<210> SEQ ID NO 13
<211> LENGTH: 6
<212> TYPE: PRT
<213> ORGANISM: Artificial sequence
<220> FEATURE:
<223> OTHER INFORMATION: chemically synthesized

<400> SEQUENCE: 13

Ile Asn Asn Ile Pro Trp
1               5

<210> SEQ ID NO 14
<211> LENGTH: 6
<212> TYPE: PRT
<213> ORGANISM: Artificial sequence
<220> FEATURE:
<223> OTHER INFORMATION: chemically synthesized

<400> SEQUENCE: 14

Asn Asn Ile Pro Trp Ser
1               5

<210> SEQ ID NO 15
<211> LENGTH: 6
<212> TYPE: PRT
<213> ORGANISM: Artificial sequence
<220> FEATURE:
<223> OTHER INFORMATION: chemically synthesized

<400> SEQUENCE: 15

Ile Asn Ile Pro Trp Ser
1               5

<210> SEQ ID NO 16
<211> LENGTH: 12
<212> TYPE: PRT
<213> ORGANISM: Artificial sequence
<220> FEATURE:
<223> OTHER INFORMATION: chemically synthesized

<400> SEQUENCE: 16

Arg Ile Asn Asn Ile Pro Trp Ser Glu Ala Met Met
1               5                   10

<210> SEQ ID NO 17
<211> LENGTH: 101
<212> TYPE: PRT
<213> ORGANISM: Nostoc ellipsosporum
<220> FEATURE:
<221> NAME/KEY: DISULFID
<222> LOCATION: (8)..(22)
<220> FEATURE:
<221> NAME/KEY: DISULFID
<222> LOCATION: (58)..(73)

<400> SEQUENCE: 17

Leu Gly Lys Phe Ser Gln Thr Cys Tyr Asn Ser Ala Ile Gln Gly Ser
1               5                   10                  15

Val Leu Thr Ser Thr Cys Glu Arg Thr Asn Gly Gly Tyr Asn Thr Ser
            20                  25                  30

Ser Ile Asp Leu Asn Ser Val Ile Glu Asn Val Asp Gly Ser Leu Lys
        35                  40                  45

Trp Gln Pro Ser Asn Phe Ile Glu Thr Cys Arg Asn Thr Gln Leu Ala
    50                  55                  60

```
Gly Ser Ser Glu Leu Ala Ala Glu Cys Lys Thr Arg Ala Gln Gln Phe
65                  70                  75                  80

Val Ser Thr Lys Ile Asn Leu Asp Asp His Ile Ala Asn Ile Asp Gly
                85                  90                  95

Thr Leu Lys Tyr Glu
            100

<210> SEQ ID NO 18
<211> LENGTH: 303
<212> TYPE: DNA
<213> ORGANISM: Nostoc ellipsosporum

<400> SEQUENCE: 18
cttggtaaat ctcccagac ctgctacaac tccgctatcc agggttccgt tctgacctcc      60
acctgcgaac gtaccaacgg tggttacaac acctcctcca tcgacctgaa ctccgttatc    120
gaaaacgttg acggttccct gaatggcag ccgtccaact tcatcgaaac ctgccgtaac     180
acccagctgg ctggttcctc cgaactggct gctgatgcaa aacccgtgc tcagcagttc     240 gtttccacca aaatcaacct ggacgaccac atcgctaaca tcgacggtac cctgaaatac    300
gaa                                                                  303

<210> SEQ ID NO 19
<211> LENGTH: 12
<212> TYPE: PRT
<213> ORGANISM: Artificial Sequence
<220> FEATURE:
<223> OTHER INFORMATION: chemically synthesized
<220> FEATURE:
<221> NAME/KEY: MISC_FEATURE
<222> LOCATION: (6)..(6)
<223> OTHER INFORMATION: (2S, 4S)-4-(4-ferrocenyl-1H-1, 2, 3-triazol-
      1-yl) pyrrolidine-2-carboxylic acid)

<400> SEQUENCE: 19

Arg Ile Asn Asn Ile Xaa Trp Ser Glu Ala Met Met
1               5                   10

<210> SEQ ID NO 20
<211> LENGTH: 16
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (6)..(6)
<223> OTHER INFORMATION: (2S, 4S)-4-(4-ferrocenyl-1H-1, 2, 3-triazol-
      1-yl) pyrrolidine-2-carboxylic acid)
<220> FEATURE:
<221> NAME/KEY: MOD_RES
<222> LOCATION: (15)..(15)
<223> OTHER INFORMATION: Orn

<400> SEQUENCE: 20

Arg Ile Asn Asn Ile Xaa Trp Ser Glu Ala Met Met Gly Gly Xaa Cys
1               5                   10                  15

<210> SEQ ID NO 21
<211> LENGTH: 5
<212> TYPE: PRT
<213> ORGANISM: Artificial sequence
<220> FEATURE:
<223> OTHER INFORMATION: chemically synthesized

<400> SEQUENCE: 21

Asn Asn Ile Pro Trp
```

```
1               5

<210> SEQ ID NO 22
<211> LENGTH: 5
<212> TYPE: PRT
<213> ORGANISM: Artificial sequence
<220> FEATURE:
<223> OTHER INFORMATION: chemically synthesized

<400> SEQUENCE: 22

Asn Ile Pro Trp Ser
1               5

<210> SEQ ID NO 23
<211> LENGTH: 6
<212> TYPE: PRT
<213> ORGANISM: Artificial sequence
<220> FEATURE:
<223> OTHER INFORMATION: chemically synthesized

<400> SEQUENCE: 23

Arg Asn Ile Pro Trp Ser
1               5

<210> SEQ ID NO 24
<211> LENGTH: 6
<212> TYPE: PRT
<213> ORGANISM: Artificial sequence
<220> FEATURE:
<223> OTHER INFORMATION: chemically synthesized

<400> SEQUENCE: 24

Glu Asn Ile Pro Trp Ser
1               5

<210> SEQ ID NO 25
<211> LENGTH: 6
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: citrulline

<400> SEQUENCE: 25

Xaa Asn Ile Pro Trp Ser
1               5

<210> SEQ ID NO 26
<211> LENGTH: 7
<212> TYPE: PRT
<213> ORGANISM: Artificial sequence
<220> FEATURE:
<223> OTHER INFORMATION: chemically synthesized
<220> FEATURE:
<221> NAME/KEY: MISC_FEATURE
<222> LOCATION: (1)..(1)
<223> OTHER INFORMATION: X is one of Arg, Glu, Citrulline, Lys or Phe

<400> SEQUENCE: 26

Xaa Asn Asn Ile Pro Trp Ser
1               5
```